US010538722B2

(12) United States Patent
Gjermansen et al.

(10) Patent No.: US 10,538,722 B2
(45) Date of Patent: Jan. 21, 2020

(54) METALLOPROTEASES AND USES THEREOF

(71) Applicant: NOVOZYMES A/S, Bagsvaerd (DK)

(72) Inventors: Morten Gjermansen, Greve (DK); Peter R. Oestergaard, Virum (DK); Jeannette Bjerre, Copenhagen SV (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 15/524,650

(22) PCT Filed: Nov. 9, 2015

(86) PCT No.: PCT/EP2015/076062
§ 371 (c)(1),
(2) Date: May 5, 2017

(87) PCT Pub. No.: WO2016/075078
PCT Pub. Date: May 19, 2016

(65) Prior Publication Data
US 2017/0342352 A1    Nov. 30, 2017

(30) Foreign Application Priority Data
Nov. 10, 2014    (EP) ..................................... 14192444

(51) Int. Cl.
*C11D 3/386* (2006.01)
*C12N 9/52* (2006.01)
*C12N 9/50* (2006.01)

(52) U.S. Cl.
CPC ............ *C11D 3/38681* (2013.01); *C12N 9/52* (2013.01); *C12Y 304/24004* (2013.01)

(58) Field of Classification Search
CPC .......... C12Y 304/24; C12Y 304/24004; C12N 9/52; C11D 3/38681; C11D 3/386
See application file for complete search history.

(56) References Cited

U.S. PATENT DOCUMENTS

| 2014/0038876 A1 | 2/2014 | Oestergaard |
| 2016/0160202 A1* | 6/2016 | Babe .................. C12N 9/52 |
| | | 435/220 |

FOREIGN PATENT DOCUMENTS

| EP | 1288282 A1 | 3/2003 |
| EP | 1852508 A2 | 11/2007 |
| WO | 00/60042 A1 | 10/2000 |
| WO | 2004/078973 A1 | 9/2004 |
| WO | 2007/044993 A2 | 4/2007 |
| WO | 2009/058518 A1 | 5/2009 |
| WO | 2014/194032 A1 | 12/2014 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003 ).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Guo et al., Protein tolerance to random amino acid change. PNAS., 2004, vol. 101 (25): 9205-9210. (Year: 2004).*
Saponins, 2 pages, http://www.ecologicalsurfactants.com/saponin/, retrieved, Mar. 13, 2014 (Year: 2014).*
Surfactants, 8 pages, http://www.rsc.org/chemistryworld/issues/2003/july/amphiphiles.asp/, retrieved Mar. 13, 2014 (Year: 2014).*
Li et al. 2011, UniProt No. F3NG17.
Puopolo et al. 2014, UniProt No. A0A021W7N8.
Lund et al, 2012, J Surfact Deterg 15, 9-21.
Stoner et al, 2004, Enzyme Microb Technol 34, 114-125.

* cited by examiner

*Primary Examiner* — Ganapathirama Raghu
(74) *Attorney, Agent, or Firm* — David Fazzolare

(57) ABSTRACT

The present invention relates to metalloproteases and the use thereof in cleaning processes, such as laundry and dish wash. The invention also relates to detergent compositions and cleaning compositions comprising a metalloprotease.

21 Claims, No Drawings
Specification includes a Sequence Listing.

SEQUENCE LISTING

<160> NUMBER OF SEQ ID NOS: 7

<210> SEQ ID NO 1
<211> LENGTH: 1659
<212> TYPE: DNA
<213> ORGANISM: Streptomyces thermoalcalitolerans
<220> FEATURE:
<221> NAME/KEY: CDS
<222> LOCATION: (1)..(1656)
<220> FEATURE:
<221> NAME/KEY: misc_feature
<222> LOCATION: (1)..(3)
<223> OTHER INFORMATION: The first amino acid (position -224) in the
      polypeptide shown in SEQ ID NO: 2 and encoded by the
      polynucleotide shown in SEQ ID NO:1 should be Met, not Val. When
      the first codon is gtg a Met is inserted though gtg normally
      codes for Val.
<220> FEATURE:
<221> NAME/KEY: sig_peptide
<222> LOCATION: (1)..(105)
<220> FEATURE:
<221> NAME/KEY: pro_peptide
<222> LOCATION: (106)..(672)
<220> FEATURE:
<221> NAME/KEY: mat_peptide
<222> LOCATION: (673)..(1656)

<400> SEQUENCE: 1

```
gtg act ccc cgc tac gcg cgt ccc aga cgc acc gcc ctg gcc ctc        45
Val Thr Pro Arg Tyr Ala Arg Pro Arg Arg Thr Ala Leu Ala Leu
        -220                -215                -210 gcc acc gcc gtc gtg gcc gga gcc ctc ctc ggc acc ggt ctg agc        90
Ala Thr Ala Val Val Ala Gly Ala Leu Leu Gly Thr Gly Leu Ser
    -205                -200                -195 acc ggc gcc tcg gcc cag ccc cag gcc ggt tcc acc ggc gcg gcc       135
Thr Gly Ala Ser Ala Gln Pro Gln Ala Gly Ser Thr Gly Ala Ala
        -190                -185                -180 ccc ctc gcc gcc gcc ccc gtc ctg ctc tcc gac gcg gag cgc acc       180
Pro Leu Ala Ala Ala Pro Val Leu Leu Ser Asp Ala Glu Arg Thr
        -175                -170                -165 tcc ctg atc cag cag gcg cag gcc gac gcc gtc ggc acc gcc cgg       225
Ser Leu Ile Gln Gln Ala Gln Ala Asp Ala Val Gly Thr Ala Arg
        -160                -155                -150 gag ata ggc ctc ggc gcc cag gag aag ctg gtc gtc aga gat gtc       270
Glu Ile Gly Leu Gly Ala Gln Glu Lys Leu Val Val Arg Asp Val
        -145                -140                -135 gtc aag gac gcc gac ggc acg gtg cac acc cgc tac gag cgc acc       315
Val Lys Asp Ala Asp Gly Thr Val His Thr Arg Tyr Glu Arg Thr
        -130                -125                -120 tac gcg ggc ctg ccc gtc ctc ggc ggc gac ctg atc gtc cac acc       360
Tyr Ala Gly Leu Pro Val Leu Gly Gly Asp Leu Ile Val His Thr
        -115                -110                -105 tcc agg acc ggc agg acc cag ggc gtc acc aag gcc acc gag gcg acc   408
Ser Arg Thr Gly Arg Thr Gln Gly Val Thr Lys Ala Thr Glu Ala Thr
        -100                -95                 -90 atc aag gtg gac acg ctc acg ccg agg atc gcc gcc gcc aag gcc gag   456
Ile Lys Val Asp Thr Leu Thr Pro Arg Ile Ala Ala Ala Lys Ala Glu
        -85                 -80                 -75 aag cag gcg gtg acc ctg gcc cgg gcg gcc ggc tcg gag aac acc acc   504
Lys Gln Ala Val Thr Leu Ala Arg Ala Ala Gly Ser Glu Asn Thr Thr
        -70                 -65                 -60 ccc gac cag gcc ccg cgc aag gtc atc tgg gcg ggc gac ggc aca ccg   552
Pro Asp Gln Ala Pro Arg Lys Val Ile Trp Ala Gly Asp Gly Thr Pro
        -55                 -50                 -45
```

```
gtc ctc gcc tac gag acg gtc gtc ggc ggc ctc cag gac gac ggc acc        600
Val Leu Ala Tyr Glu Thr Val Val Gly Gly Leu Gln Asp Asp Gly Thr
-40             -35             -30             -25 ccg aac gaa ctg cac gtc atc acc gac gcg acc acc ggc gag aag ctg        648
Pro Asn Glu Leu His Val Ile Thr Asp Ala Thr Thr Gly Glu Lys Leu
        -20             -15             -10 tac gag tac cag ggc gtc gtg aac ggc acc ggc aga acc ctg tac tcg        696
Tyr Glu Tyr Gln Gly Val Val Asn Gly Thr Gly Arg Thr Leu Tyr Ser
        -5              -1  1               5 ggc acc gtc acc ctc tcc acc acc cgg tcg gga tcg acg tac cag ctg        744
Gly Thr Val Thr Leu Ser Thr Thr Arg Ser Gly Ser Thr Tyr Gln Leu
        10              15              20 tac gac acc acg cgc ggc ggc cac cgg acg tac aac ctg gcc cgc ggc        792
Tyr Asp Thr Thr Arg Gly Gly His Arg Thr Tyr Asn Leu Ala Arg Gly
25              30              35              40 acc tcc ggc acc ggc acc ctg ttc acc gac gcg gac gac gtg tgg ggc        840
Thr Ser Gly Thr Gly Thr Leu Phe Thr Asp Ala Asp Asp Val Trp Gly
                45              50              55 acc ggc acc gcc tcc agt tcc agc agc gac cag acg gcc gcc gcc gac        888
Thr Gly Thr Ala Ser Ser Ser Ser Ser Asp Gln Thr Ala Ala Ala Asp
        60              65              70 gcc gcc tac ggc gcc cag gtc acc tgg gac ttc tac aag aac gtc ttc        936
Ala Ala Tyr Gly Ala Gln Val Thr Trp Asp Phe Tyr Lys Asn Val Phe
        75              80              85 ggc cgc aac ggc atc agg aac aac ggg acg gcc gcc tac tca cgg gtc        984
Gly Arg Asn Gly Ile Arg Asn Asn Gly Thr Ala Ala Tyr Ser Arg Val
        90              95              100 cac tac ggc aac aac tac atc aac gcc ttc tgg tcc gac agc tgc ttc       1032
His Tyr Gly Asn Asn Tyr Ile Asn Ala Phe Trp Ser Asp Ser Cys Phe
105             110             115             120 tgc atg acc tac ggc gac ggc gcg ggc aac gtc aag ccg ctg acc tcg       1080
Cys Met Thr Tyr Gly Asp Gly Ala Gly Asn Val Lys Pro Leu Thr Ser
                125             130             135 ctg gac gtg gcc ggc cac gag atg tcc cac ggc ctc acc tcc tac acc       1128
Leu Asp Val Ala Gly His Glu Met Ser His Gly Leu Thr Ser Tyr Thr
        140             145             150 gcg ggg ctg cgg tac tcc ggc gag tcc ggc ggg ctc aac gag gcc acc       1176
Ala Gly Leu Arg Tyr Ser Gly Glu Ser Gly Gly Leu Asn Glu Ala Thr
        155             160             165 tcc gac atc ttc ggc acc ggc gtg gag ttc tac gcc aac aac gcc tcc       1224
Ser Asp Ile Phe Gly Thr Gly Val Glu Phe Tyr Ala Asn Asn Ala Ser
170             175             180 gac ccc ggt gac tac ctc atc ggc gag aag atc gac atc aac ggc aac       1272
Asp Pro Gly Asp Tyr Leu Ile Gly Glu Lys Ile Asp Ile Asn Gly Asn
185             190             195             200 ggc acc ccg ctg cgc tac atg gac agg ccc agc aag gac ggc gcc tcc       1320
Gly Thr Pro Leu Arg Tyr Met Asp Arg Pro Ser Lys Asp Gly Ala Ser
        205             210             215 gcc gac tac tgg tcc tcc ggc gtg ggc aac agg gac gtg cac tac tcg       1368
Ala Asp Tyr Trp Ser Ser Gly Val Gly Asn Arg Asp Val His Tyr Ser
        220             225             230 tcc ggc gtc gcg aac cac ttc ttc tac ctc ctc gcg gag ggc agc gga       1416
Ser Gly Val Ala Asn His Phe Phe Tyr Leu Leu Ala Glu Gly Ser Gly
        235             240             245 gcg aag acg atc aac ggc gtc agc tac aac tcg ccg acg tac gac ggc       1464
Ala Lys Thr Ile Asn Gly Val Ser Tyr Asn Ser Pro Thr Tyr Asp Gly
250             255             260 tcc agg atc acc ggc atc ggc cgc gac aag gcg ctg cag atc tgg tac       1512
Ser Arg Ile Thr Gly Ile Gly Arg Asp Lys Ala Leu Gln Ile Trp Tyr
265             270             275             280
```

```
aag gcg ctg acc acg tac atg acg tcg acc acc acc tac aag ggc gcc    1560
Lys Ala Leu Thr Thr Tyr Met Thr Ser Thr Thr Thr Tyr Lys Gly Ala
                285                 290                 295 cgc acg gcg acc ctg aac gcg gcg gcg ctg tac ggc tcc ggc agc        1608
Arg Thr Ala Thr Leu Asn Ala Ala Ala Leu Tyr Gly Ser Gly Ser
            300                 305                 310 acc gag tac aac acg gtg gcg gcg gcc tgg acc gcg gtc aac gtc acc    1656
Thr Glu Tyr Asn Thr Val Ala Ala Ala Trp Thr Ala Val Asn Val Thr
        315                 320                 325 tga                                                                 1659

<210> SEQ ID NO 2
<211> LENGTH: 552
<212> TYPE: PRT
<213> ORGANISM: Streptomyces thermoalcalitolerans

<400> SEQUENCE: 2

Val Thr Pro Arg Tyr  Ala Arg Pro Arg Arg  Thr Ala Leu Ala Leu
                -220                -215                 -210

Ala Thr Ala Val Val  Ala Gly Ala Leu Leu  Gly Thr Gly Leu Ser
                -205                -200                 -195

Thr Gly Ala Ser Ala  Gln Pro Gln Ala Gly  Ser Thr Gly Ala Ala
                -190                -185                 -180

Pro Leu Ala Ala Ala  Pro Val Leu Leu Ser  Asp Ala Glu Arg Thr
                -175                -170                 -165

Ser Leu Ile Gln Gln  Ala Gln Ala Asp Ala  Val Gly Thr Ala Arg
                -160                -155                 -150

Glu Ile Gly Leu Gly  Ala Gln Glu Lys Leu  Val Val Arg Asp Val
                -145                -140                 -135

Val Lys Asp Ala Asp  Gly Thr Val His Thr  Arg Tyr Glu Arg Thr
                -130                -125                 -120

Tyr Ala Gly Leu Pro  Val Leu Gly Gly Asp  Leu Ile Val His Thr
                -115                -110                 -105

Ser Arg Thr Gly Arg  Thr Gln Gly Val Thr  Lys Ala Thr Glu Ala Thr
                -100                 -95                  -90

Ile Lys Val Asp Thr  Leu Thr Pro Arg Ile  Ala Ala Lys Ala Glu
                 -85                 -80                  -75

Lys Gln Ala Val Thr  Leu Ala Arg Ala Ala  Gly Ser Glu Asn Thr Thr
                 -70                 -65                  -60

Pro Asp Gln Ala Pro  Arg Lys Val Ile Trp  Ala Gly Asp Gly Thr Pro
                 -55                 -50                  -45

Val Leu Ala Tyr Glu  Thr Val Val Gly Gly  Leu Gln Asp Asp Gly Thr
-40                  -35                  -30                  -25

Pro Asn Glu Leu His  Val Ile Thr Asp Ala  Thr Thr Gly Glu Lys Leu
                 -20                 -15                  -10

Tyr Glu Tyr Gln Gly  Val Val Asn Gly Thr  Gly Arg Thr Leu Tyr Ser
                  -5                 -1 1                    5

Gly Thr Val Thr Leu  Ser Thr Thr Arg Ser  Gly Ser Thr Tyr Gln Leu
                  10                  15                   20

Tyr Asp Thr Thr Arg  Gly Gly His Arg Thr  Tyr Asn Leu Ala Arg Gly
25                   30                   35                   40

Thr Ser Gly Thr Gly  Thr Leu Phe Thr Asp  Ala Asp Asp Val Trp Gly
                  45                  50                   55

Thr Gly Thr Ala Ser  Ser Ser Ser Ser Asp  Gln Thr Ala Ala Ala Asp
                  60                  65                   70
```

-continued

```
Ala Ala Tyr Gly Ala Gln Val Thr Trp Asp Phe Tyr Lys Asn Val Phe
         75                  80                  85
Gly Arg Asn Gly Ile Arg Asn Asn Gly Thr Ala Ala Tyr Ser Arg Val
 90                  95                 100
His Tyr Gly Asn Asn Tyr Ile Asn Ala Phe Trp Ser Asp Ser Cys Phe
105                 110                 115                 120
Cys Met Thr Tyr Gly Asp Gly Ala Gly Asn Val Lys Pro Leu Thr Ser
             125                 130                 135
Leu Asp Val Ala Gly His Glu Met Ser His Gly Leu Thr Ser Tyr Thr
             140                 145                 150
Ala Gly Leu Arg Tyr Ser Gly Glu Ser Gly Gly Leu Asn Glu Ala Thr
         155                 160                 165
Ser Asp Ile Phe Gly Thr Gly Val Glu Phe Tyr Ala Asn Asn Ala Ser
         170                 175                 180
Asp Pro Gly Asp Tyr Leu Ile Gly Glu Lys Ile Asp Ile Asn Gly Asn
185                 190                 195                 200
Gly Thr Pro Leu Arg Tyr Met Asp Arg Pro Ser Lys Asp Gly Ala Ser
             205                 210                 215
Ala Asp Tyr Trp Ser Ser Gly Val Gly Asn Arg Asp Val His Tyr Ser
         220                 225                 230
Ser Gly Val Ala Asn His Phe Phe Tyr Leu Leu Ala Glu Gly Ser Gly
         235                 240                 245
Ala Lys Thr Ile Asn Gly Val Ser Tyr Asn Ser Pro Thr Tyr Asp Gly
         250                 255                 260
Ser Arg Ile Thr Gly Ile Gly Arg Asp Lys Ala Leu Gln Ile Trp Tyr
265                 270                 275                 280
Lys Ala Leu Thr Thr Tyr Met Thr Ser Thr Thr Tyr Lys Gly Ala
             285                 290                 295
Arg Thr Ala Thr Leu Asn Ala Ala Ala Leu Tyr Gly Ser Gly Ser
         300                 305                 310
Thr Glu Tyr Asn Thr Val Ala Ala Ala Trp Thr Ala Val Asn Val Thr
         315                 320                 325
```

<210> SEQ ID NO 3
<211> LENGTH: 1551
<212> TYPE: DNA
<213> ORGANISM: Lysobacter capsici
<220> FEATURE:
<221> NAME/KEY: CDS
<222> LOCATION: (1)..(1548)
<220> FEATURE:
<221> NAME/KEY: sig_peptide
<222> LOCATION: (1)..(69)
<220> FEATURE:
<221> NAME/KEY: pro-peptide
<222> LOCATION: (70)..(678)
<220> FEATURE:
<221> NAME/KEY: mat_peptide
<222> LOCATION: (679)..(1548)

<400> SEQUENCE: 3

```
atg aag cgc aac gta tcg gta ctg tcc ttc gct gtc tcg atc gcc         45
Met Lys Arg Asn Val Ser Val Leu Ser Phe Ala Val Ser Ile Ala
    -225                -220                -215 ctc gcc gcc ggc gcc gcc ggc gcc gcc caa cgc gtg gat ctg cac         90
Leu Ala Ala Gly Ala Ala Gly Ala Ala Gln Arg Val Asp Leu His
    -210                -205                -200 ggc gtc gac gtc gtc aaa ctc aac cag cag ttc cag gcc gcc acc        135
Gly Val Asp Val Val Lys Leu Asn Gln Gln Phe Gln Ala Ala Thr
    -195                -190                -185
```

| | | | | | | | | | | | | | | |
|---|---|---|---|---|---|---|---|---|---|---|---|---|---|---|
| gcc | aag | tcc | ggg | gtc | gcc | gcc | aag | gcc | aac | gtg | cgc | cac | gcc | gag | 180 |
| Ala | Lys | Ser | Gly | Val | Ala | Ala | Lys | Ala | Asn | Val | Arg | His | Ala | Glu | |
| | -180 | | | | -175 | | | | -170 | | | | | | |

```
gcc aag tcc ggg gtc gcc gcc aag gcc aac gtg cgc cac gcc gag       180
Ala Lys Ser Gly Val Ala Ala Lys Ala Asn Val Arg His Ala Glu
    -180            -175            -170 ctg atc gcg ctc gat gcc gac tcg acc ctg acc tcg ctc aag agc       225
Leu Ile Ala Leu Asp Ala Asp Ser Thr Leu Thr Ser Leu Lys Ser
    -165            -160            -155 agc cag gat gcc gac ggc tcg caa aac cat cgc tac caa caa agc       270
Ser Gln Asp Ala Asp Gly Ser Gln Asn His Arg Tyr Gln Gln Ser
    -150            -145            -140 ttc cgc ggc gtg ccg gtg ttc ggc gag cac gtg atc gtg cgc gag       315
Phe Arg Gly Val Pro Val Phe Gly Glu His Val Ile Val Arg Glu
    -135            -130            -125 gac gcc aag ggc aac gta cgc gcc ctg ttc ggc cgc tcg gtc gcc       360
Asp Ala Lys Gly Asn Val Arg Ala Leu Phe Gly Arg Ser Val Ala
    -120            -115            -110 ggc atc gcc gcc gat ctg ccg aag ctc gac gcc aag ctc agc gcc gcc   408
Gly Ile Ala Ala Asp Leu Pro Lys Leu Asp Ala Lys Leu Ser Ala Ala
    -105            -100            -95 cag gcc ttg agc ctg gcc aag ggc gcc acg ctc ggc aag cgc gcg gcg   456
Gln Ala Leu Ser Leu Ala Lys Gly Ala Thr Leu Gly Lys Arg Ala Ala
-90             -85             -80             -75 acg ctg cag gtc cgc aac gag aac agc cgc aag gtg atc tac ctc gac   504
Thr Leu Gln Val Arg Asn Glu Asn Ser Arg Lys Val Ile Tyr Leu Asp
        -70             -65             -60 gac gcc gat cgc gcc cat ctg gcc tat gcg gtc gac tac ttc gcc gat   552
Asp Ala Asp Arg Ala His Leu Ala Tyr Ala Val Asp Tyr Phe Ala Asp
            -55             -50             -45 gcg ccc agc ggc ggc gaa ccc agc cgt ccg ttc gcg atc gtc gac gcc   600
Ala Pro Ser Gly Gly Glu Pro Ser Arg Pro Phe Ala Ile Val Asp Ala
        -40             -35             -30 aac agc ggc aag gtg ctc aag cag tgg gaa ggc ctc aac cac gag caa   648
Asn Ser Gly Lys Val Leu Lys Gln Trp Glu Gly Leu Asn His Glu Gln
    -25             -20             -15 gtc ggt acc ggc ccc ggc ggc aac cag aag atc ggc cag tac gaa tac   696
Val Gly Thr Gly Pro Gly Gly Asn Gln Lys Ile Gly Gln Tyr Glu Tyr
-10             -5              -1  1           5 ggc agc ggc ggc cgc ccg ttc ctc gac gtc acc cgc agc ggc agc acc   744
Gly Ser Gly Gly Arg Pro Phe Leu Asp Val Thr Arg Ser Gly Ser Thr
        10              15              20 tat acg ttc aac acc ccg aac gtg aag acg gtc aat ctc aac cac ggc   792
Tyr Thr Phe Asn Thr Pro Asn Val Lys Thr Val Asn Leu Asn His Gly
        25              30              35 acc agc ggc tcc acc gcc tac tcg tac gcc ggc ccg cgc aac acg gtc   840
Thr Ser Gly Ser Thr Ala Tyr Ser Tyr Ala Gly Pro Arg Asn Thr Val
40              45              50 aag acc atc aac ggc gcc tac tcg ccg ctc aac gat gcg cac tat tac   888
Lys Thr Ile Asn Gly Ala Tyr Ser Pro Leu Asn Asp Ala His Tyr Tyr
55              60              65              70 ggc aag gtc gtg ttc gac acc tac cag gcc tat ctg ggc atc tcg ccg   936
Gly Lys Val Val Phe Asp Thr Tyr Gln Ala Tyr Leu Gly Ile Ser Pro
            75              80              85 ctg acc ttc cag ctg acc ctg cgc gtg cat tac agc aac aac tac gag   984
Leu Thr Phe Gln Leu Thr Leu Arg Val His Tyr Ser Asn Asn Tyr Glu
        90              95              100 aac gcg ttc tgg gac ggc cgc gcg ctg acc ttc ggc gac ggc cgc acc   1032
Asn Ala Phe Trp Asp Gly Arg Ala Leu Thr Phe Gly Asp Gly Arg Thr
        105             110             115 acc ttc tat ccg ctg gtc tcg ctc gac gtg gtc gcg cac gag gcc tcg   1080
Thr Phe Tyr Pro Leu Val Ser Leu Asp Val Val Ala His Glu Ala Ser
        120             125             130
```

| | | |
|---|---|---|
| cac ggc ttc acc gaa cag cag tcg ggc ctg atc tac tcc ggc cag tcc<br>His Gly Phe Thr Glu Gln Gln Ser Gly Leu Ile Tyr Ser Gly Gln Ser<br>135                   140                   145                  150 | 1128 | |
| ggc ggc atc aac gaa tcg ttc tcc gac atc gcc ggc gaa gcg gcc gag<br>Gly Gly Ile Asn Glu Ser Phe Ser Asp Ile Ala Gly Glu Ala Ala Glu<br>                 155                   160                   165 | 1176 | |
| ttc tac gcg cgc ggc agc aac gat ttc ctg gtc ggc gcc gac atc ttc<br>Phe Tyr Ala Arg Gly Ser Asn Asp Phe Leu Val Gly Ala Asp Ile Phe<br>170                   175                   180 | 1224 | |
| aag gcc agc ggc cgc gcg ctg cgc tac ttc gcc aac ccg ccg caa gac<br>Lys Ala Ser Gly Arg Ala Leu Arg Tyr Phe Ala Asn Pro Pro Gln Asp<br>                 185                   190                   195 | 1272 | |
| gga cgc tcg atc ggc cac gcc agc aac tac acc agc gga ctg gac gtg<br>Gly Arg Ser Ile Gly His Ala Ser Asn Tyr Thr Ser Gly Leu Asp Val<br>200                   205                   210 | 1320 | |
| cac tac tcc tcg ggc gtg ttc aac aag gcc ttc tac atc ctg gcc aac<br>His Tyr Ser Ser Gly Val Phe Asn Lys Ala Phe Tyr Ile Leu Ala Asn<br>215                   220                   225                  230 | 1368 | |
| aag ccg ggc tgg ggc acg gtc aag gcg ttc aag gcc ttc gcc aag gcc<br>Lys Pro Gly Trp Gly Thr Val Lys Ala Phe Lys Ala Phe Ala Lys Ala<br>                 235                   240                   245 | 1416 | |
| aac aag gac tac tgg acg ccg agc acc aac ttc aac cag ggc ggc acc<br>Asn Lys Asp Tyr Trp Thr Pro Ser Thr Asn Phe Asn Gln Gly Gly Thr<br>250                   255                   260 | 1464 | |
| ggc gtg cgt cag gcc gcg gcc gac ctg ggc tac agc acc gcc gat gtg<br>Gly Val Arg Gln Ala Ala Ala Asp Leu Gly Tyr Ser Thr Ala Asp Val<br>                 265                   270                   275 | 1512 | |
| gtc aac gcg ttc tcc cag gtg ggc gtg acc gcg caa taa<br>Val Asn Ala Phe Ser Gln Val Gly Val Thr Ala Gln<br>280                   285                   290 | 1551 | |

<210> SEQ ID NO 4
<211> LENGTH: 516
<212> TYPE: PRT
<213> ORGANISM: Lysobacter capsici

<400> SEQUENCE: 4

Met Lys Arg Asn Val Ser Val Leu Ser Phe Ala Val Ser Ile Ala
    -225                 -220                -215

Leu Ala Ala Gly Ala Ala Gly Ala Ala Gln Arg Val Asp Leu His
    -210                -205                -200

Gly Val Asp Val Val Lys Leu Asn Gln Gln Phe Gln Ala Ala Thr
    -195                -190                -185

Ala Lys Ser Gly Val Ala Ala Lys Ala Asn Val Arg His Ala Glu
    -180                -175                -170

Leu Ile Ala Leu Asp Ala Asp Ser Thr Leu Thr Ser Leu Lys Ser
    -165                -160                -155

Ser Gln Asp Ala Asp Gly Ser Gln Asn His Arg Tyr Gln Gln Ser
    -150                -145                -140

Phe Arg Gly Val Pro Val Phe Gly Glu His Val Ile Val Arg Glu
    -135                -130                -125

Asp Ala Lys Gly Asn Val Arg Ala Leu Phe Gly Arg Ser Val Ala
    -120                -115                -110

Gly Ile Ala Ala Asp Leu Pro Lys Leu Asp Ala Lys Leu Ser Ala Ala
    -105                -100                -95

```
Gln Ala Leu Ser Leu Ala Lys Gly Ala Thr Leu Gly Lys Arg Ala Ala
-90                 -85                 -80                 -75

Thr Leu Gln Val Arg Asn Glu Asn Ser Arg Lys Val Ile Tyr Leu Asp
            -70                 -65                 -60

Asp Ala Asp Arg Ala His Leu Ala Tyr Ala Val Asp Tyr Phe Ala Asp
            -55                 -50                 -45

Ala Pro Ser Gly Gly Glu Pro Ser Arg Pro Phe Ala Ile Val Asp Ala
        -40                 -35                         -30

Asn Ser Gly Lys Val Leu Lys Gln Trp Glu Gly Leu Asn His Glu Gln
    -25                 -20                 -15

Val Gly Thr Gly Pro Gly Asn Gln Lys Ile Gly Gln Tyr Glu Tyr
-10             -5                  -1  1                   5

Gly Ser Gly Gly Arg Pro Phe Leu Asp Val Thr Arg Ser Gly Ser Thr
            10                  15                  20

Tyr Thr Phe Asn Thr Pro Asn Val Lys Thr Val Asn Leu Asn His Gly
        25                  30                  35

Thr Ser Gly Ser Thr Ala Tyr Ser Tyr Ala Gly Pro Arg Asn Thr Val
    40                  45                  50

Lys Thr Ile Asn Gly Ala Tyr Ser Pro Leu Asn Asp Ala His Tyr Tyr
55              60                  65                  70

Gly Lys Val Val Phe Asp Thr Tyr Gln Ala Tyr Leu Gly Ile Ser Pro
                75                  80                  85

Leu Thr Phe Gln Leu Thr Leu Arg Val His Tyr Ser Asn Asn Tyr Glu
            90                  95                  100

Asn Ala Phe Trp Asp Gly Arg Ala Leu Thr Phe Gly Asp Gly Arg Thr
            105                 110                 115

Thr Phe Tyr Pro Leu Val Ser Leu Asp Val Val Ala His Glu Ala Ser
        120                 125                 130

His Gly Phe Thr Glu Gln Gln Ser Gly Leu Ile Tyr Ser Gly Gln Ser
135             140                 145                 150

Gly Gly Ile Asn Glu Ser Phe Ser Asp Ile Ala Gly Glu Ala Ala Glu
            155                 160                 165

Phe Tyr Ala Arg Gly Ser Asn Asp Phe Leu Val Gly Ala Asp Ile Phe
        170                 175                 180

Lys Ala Ser Gly Arg Ala Leu Arg Tyr Phe Ala Asn Pro Pro Gln Asp
        185                 190                 195

Gly Arg Ser Ile Gly His Ala Ser Asn Tyr Thr Ser Gly Leu Asp Val
        200                 205                 210

His Tyr Ser Ser Gly Val Phe Asn Lys Ala Phe Tyr Ile Leu Ala Asn
215             220                 225                 230

Lys Pro Gly Trp Gly Thr Val Lys Ala Phe Lys Ala Phe Ala Lys Ala
            235                 240                 245

Asn Lys Asp Tyr Trp Thr Pro Ser Thr Asn Phe Asn Gln Gly Gly Thr
        250                 255                 260

Gly Val Arg Gln Ala Ala Ala Asp Leu Gly Tyr Ser Thr Ala Asp Val
        265                 270                 275

Val Asn Ala Phe Ser Gln Val Gly Val Thr Ala Gln
280                 285                 290

<210> SEQ ID NO 5
<211> LENGTH: 27
<212> TYPE: PRT
<213> ORGANISM: Bacillus clausii
```

-continued

<400> SEQUENCE: 5

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 6
<211> LENGTH: 300
<212> TYPE: PRT
<213> ORGANISM: Bacillus amyloliquefaciens

<400> SEQUENCE: 6

Ala Ala Thr Thr Gly Thr Gly Thr Leu Lys Gly Lys Thr Val Ser
1               5                   10                  15

Leu Asn Ile Ser Ser Glu Ser Gly Lys Tyr Val Leu Arg Asp Leu Ser
                20                  25                  30

Lys Pro Thr Gly Thr Gln Ile Ile Thr Tyr Asp Leu Gln Asn Arg Glu
            35                  40                  45

Tyr Asn Leu Pro Gly Thr Leu Val Ser Ser Thr Asn Gln Phe Thr
    50                  55                  60

Thr Ser Ser Gln Arg Ala Ala Val Asp Ala His Tyr Asn Leu Gly Lys
65                  70                  75                  80

Val Tyr Asp Tyr Phe Tyr Gln Lys Phe Asn Arg Asn Ser Tyr Asp Asn
                85                  90                  95

Lys Gly Gly Lys Ile Val Ser Ser Val His Tyr Gly Ser Arg Tyr Asn
            100                 105                 110

Asn Ala Ala Trp Ile Gly Asp Gln Met Ile Tyr Gly Asp Gly Asp Gly
        115                 120                 125

Ser Phe Phe Ser Pro Leu Ser Gly Ser Met Asp Val Thr Ala His Glu
    130                 135                 140

Met Thr His Gly Val Thr Gln Glu Thr Ala Asn Leu Asn Tyr Glu Asn
145                 150                 155                 160

Gln Pro Gly Ala Leu Asn Glu Ser Phe Ser Asp Val Phe Gly Tyr Phe
                165                 170                 175

Asn Asp Thr Glu Asp Trp Asp Ile Gly Glu Asp Ile Thr Val Ser Gln
            180                 185                 190

Pro Ala Leu Arg Ser Leu Ser Asn Pro Thr Lys Tyr Gly Gln Pro Asp
        195                 200                 205

Asn Phe Lys Asn Tyr Lys Asn Leu Pro Asn Thr Asp Ala Gly Asp Tyr
    210                 215                 220

Gly Gly Val His Thr Asn Ser Gly Ile Pro Asn Lys Ala Ala Tyr Asn
225                 230                 235                 240

Thr Ile Thr Lys Ile Gly Val Asn Lys Ala Glu Gln Ile Tyr Tyr Arg
                245                 250                 255

Ala Leu Thr Val Tyr Leu Thr Pro Ser Ser Thr Phe Lys Asp Ala Lys
            260                 265                 270

Ala Ala Leu Ile Gln Ser Ala Arg Asp Leu Tyr Gly Ser Gln Asp Ala
        275                 280                 285

Ala Ser Val Glu Ala Ala Trp Asn Ala Val Gly Leu
    290                 295                 300

<210> SEQ ID NO 7
<211> LENGTH: 269
<212> TYPE: PRT
<213> ORGANISM: Bacillus clausii

```
<400> SEQUENCE: 7

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

METALLOPROTEASES AND USES THEREOF

CROSS-REFERENCE TO RELATED APPLICATIONS

This application is a 35 U.S.C. 371 national application of PCT/EP2015/076062 filed Nov. 9, 2015, which claims priority or the benefit under 35 U.S.C. 119 of European application no. 14192444.9 filed Nov. 10, 2014, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to metalloproteases (E.C 3.4.24) from *Streptomyces thermoalcalitolerans* and *Lysobacter capsici*, as well as the use thereof in cleaning processes, such as dish wash and laundry. The invention further relates to cleaning and/or detergent compositions comprising metalloproteases.

BACKGROUND OF THE INVENTION

The detergent industry has for more than 30 years implemented different enzymes in detergent formulations, most commonly used enzymes includes proteases, amylases and lipases each adapted for removing various types of stains. In addition to the enzymes detergent compositions typically include a complex combination of ingredients. For example, most cleaning products include surfactant system, bleaching agents or builders.

The proteases are one of the standard ingredients of all kinds of detergents ranging from those used for household laundering to reagents used for cleaning contact lenses or dentures. In textile laundry the proteases remove protein stains such as grass, blood, egg and human sweat. These organic stains have a tendency to adhere strongly to textile fibres. Proteases hydrolyse the proteins in the stains and break them down into more soluble polypeptides or free amino acids.

Alkaline serine proteases are the most important group of protease exploited commercially in the detergent industry. Subtilisins are a prototypical group of bacterial serine proteases used extensively in detergents due to their stability and activity at high temperature and alkaline pH. A commercially important subtilisin used extensively in the detergent industry is Savinase®.

New interest in properties such as low-temperature performance and development of new detergent compositions has led to renewed interest for new proteases and other types of detergent enzymes. The search for new proteases is not limited to subtilisins, but is also directed at finding new protease backbones suitable for application in detergent products.

Metalloproteases is a group of proteases which has not yet been commercially applied in detergent industry, mainly due to low stability in detergent compositions as well as under the conditions during the wash process. Metalloproteases are proteolytic enzymes having an absolute requirement for metal ion for their activity. Most metalloproteases are zinc-dependent, although some use other transition metals. Metalloproteases have been widely used in different industries like food and brewing industry. One group of metalloproteases is the M4 family metalloproteases which have been used in various applications. For example, the M4 metalloprotease from *Bacillus amyloliquefaciens*, also known as Neutrase®, has been used for many years as an additive in various foods and feed products. This metalloprotease has also been described for use in detergent and cleaning compositions and processes e.g., in WO 2007/044993, use of storage-stable metalloproteases in detergent or WO 2009/058518, and EP 1 288 282, which describes a blend of a metalloprotease and a serine protease for use in dish washing. WO 2000/60042 also describes detergent compositions containing a metalloprotease. WO 2007/044993 describes the use of the metalloproteases Neutrase® and/or "NprE" for use in detergent applications. M4 metalloproteases have a pH optimum mainly at neutral pH.

Unfortunately, metalloproteases are unstable in conventional detergent compositions and under conventional wash conditions. Thus, the use of metalloproteases in detergents and in wash and cleaning processes has not yet been commercialized.

Therefore there remains a need for metalloproteases having increased stability in detergent compositions and/or under wash conditions. The present invention is directed to providing such enzymes.

A nucleotide sequence encoding a predicted metallopeptidase has been identified in *Streptomyces griseoaurantiacus*. The encoded protein UNIPROT:F3NG17 is 79% identical to the metalloprotease of the present invention shown in SEQ ID NO:2.

A nucleotide sequence encoding a predicted uncharacterized protein has been identified in *Lysobacter capsici*. The encoded protein UNIPROT:A0A021W7N8 is 99.2% identical to the metalloprotease of the present invention shown in SEQ ID NO:4.

SUMMARY OF THE INVENTION

The present invention provides polypeptides having protease activity and polynucleotides encoding the polypeptides. The polypeptides are M4 metalloproteases having improved wash performance. In particular the metalloproteases of the present invention have improved wash performance in powder detergent wash solution. The improved wash performance is believed to be caused by increased stability of the polypeptide under the alkaline conditions present in the powder detergent wash solution.

Accordingly, the present invention relates to an isolated polypeptide having protease activity selected from the group consisting of:

a. a polypeptide having at least 85% sequence identity, at least 86% sequence identity, at least 87% sequence identity, at least 88% sequence identity, at least 89% sequence identity, at least 90% sequence identity, at least 91% sequence identity, at least 93% sequence identity, at least 94% sequence identity, at least 95% sequence identity, at least 96% sequence identity, at least 97% sequence identity, at least 98% sequence identity, at least 99% sequence identity, at least 99.1% sequence identity, at least 99.2% sequence identity, at least 99.3% sequence identity, at least 99.4% sequence identity, at least 99.5% sequence identity, at least 99.6% sequence identity, at least 99.7% sequence identity, at least 99.8% sequence identity, at least 99.9% sequence identity or even 100% sequence identity to the mature polypeptide of SEQ ID NO: 2, or the mature polypeptide of SEQ ID NO: 4;
b. a polypeptide encoded by a polynucleotide that hybridizes under medium stringency conditions with (i) the mature polypeptide coding sequence of SEQ ID NO: 1 or SEQ ID NO: 3 or (ii) the full-length complementary strand of (i);
c. a polypeptide encoded by a polynucleotide having at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, at least 99.1% sequence identity, at least 99.2% sequence identity, at least 99.3% sequence identity, at least 99.4% sequence identity, at least 99.5% sequence identity, at least 99.6% sequence identity, at least 99.7% sequence identity, at least 99.8% sequence identity, at least 99.9% sequence identity or even 100% sequence identity to the mature polypeptide coding sequence of SEQ ID NO: 1 or of SEQ ID NO: 3;
d. a variant comprising a substitution, deletion, and/or insertion of one or more (e.g. several) amino acids of the mature polypeptide of SEQ ID NO: 2, or the mature polypeptide of SEQ ID NO: 4; and
e. a fragment of a polypeptide of (a), (b), (c), or (d) that has protease activity.

The invention further relates to compositions comprising an isolated polypeptide having protease activity selected from the group consisting of:
a. a polypeptide having at least 60% sequence identity, at least 65% sequence identity, at least 70% sequence identity, at least 75% sequence identity, at least 80% sequence identity, at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity or at least 99% sequence identity to the mature polypeptide of SEQ ID NO: 2, or the mature polypeptide of SEQ ID NO: 4;
b. a polypeptide encoded by a polynucleotide that hybridizes under high stringency conditions with (i) the mature polypeptide coding sequence of SEQ ID NO: 1 or of SEQ ID NO: 3 or (ii) the full-length complementary strand of (i);
c. a polypeptide encoded by a polynucleotide having at least 60% sequence identity, at least 65% sequence identity, at least 70% sequence identity, at least 75% sequence identity, at least 80% sequence identity, at least 85% sequence identity, at least 90% sequence identity, at least 92% sequence identity, at least 93% sequence identity, at least 94% sequence identity, at least 95% sequence identity, at least 96% sequence identity, at least 97% sequence identity, at least 98% sequence identity or at least 99% sequence identity to the mature polypeptide coding sequence of SEQ ID NO: 1 or of SEQ ID NO: 3;
d. a variant comprising a substitution, deletion, and/or insertion of one or more (e.g. several) amino acids of the mature polypeptide of SEQ ID NO: 2, or the mature polypeptide of SEQ ID NO: 4; and
e. a fragment of a polypeptide of (a), (b), (c), or (d) that has protease activity.

The invention further relates to such compositions which are in particular detergent compositions, and to the use of such composition in a cleaning process such as laundry and hard surface cleaning e.g. automated dish wash.

In a particular embodiment, the invention relates to polynucleotides encoding the polypeptides of the invention, constructs, expression vectors and host cells comprising such polynucleotides and the use thereof for the production of the polypeptide of the invention.

Overview of Sequence Listing

SEQ ID NO: 1: DNA sequence of metalloprotease from *Streptomyces thermoalcalitolerans*.
SEQ ID NO: 2: The amino acid sequence as deduced from SEQ ID NO: 1.
SEQ ID NO: 3: DNA sequence of metalloprotease from *Lysobacter capsici*.
SEQ ID NO: 4: The amino acid sequence as deduced from SEQ ID NO: 3.
SEQ ID NO: 5: *Bacillus clausii* secretion signal
SEQ ID NO: 6: *Bacillus amyloliquefaciens* metalloprotease Uniprot: P06832 (Neutrase®)
SEQ ID NO: 7: *Bacillus clausii* serine protease Uniprot: P29600 (Savinase®)

DETAILED DESCRIPTION OF THE INVENTION

Definitions

"Polypeptides having protease activity" polypeptides having protease activity, or proteases, are sometimes also designated peptidases, proteinases, peptide hydrolases, or proteolytic enzymes. Proteases may be of the exo-type that hydrolyses peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. The present invention provides for the use of polypeptides having protease activity in detergent compositions. It also provides polynucleotides encoding the polypeptides. The protease of the invention is a metalloprotease of the MEOPS family M4.

In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the mature polypeptide of SEQ ID NO: 2.

In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the mature polypeptide of SEQ ID NO: 2.

In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 2.

In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the mature polypeptide of SEQ ID NO: 2.

In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the mature polypeptide of SEQ ID NO: 2.

In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the mature polypeptide of SEQ ID NO: 2.

In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the mature polypeptide of SEQ ID NO: 2.

In a particular embodiment the invention relates to polypeptides having a sequence identity to the mature polypeptide of SEQ ID NO: 4 of at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9% or even 100%, and wherein the polypeptide has at least at least 70% of the protease activity of the mature polypeptide of SEQ ID NO: 4.

In a particular embodiment the invention relates to polypeptides having a sequence identity to the mature polypeptide of SEQ ID NO: 4 of at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9% or even 100%, and wherein the polypeptide has at least at least 75% of the protease activity of the mature polypeptide of SEQ ID NO: 4.

In a particular embodiment the invention relates to polypeptides having a sequence identity to the mature polypeptide of SEQ ID NO: 4 of at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9% or even 100%, and wherein the polypeptide has at least at least 80% of the protease activity of the mature polypeptide of SEQ ID NO: 4.

In a particular embodiment the invention relates to polypeptides having a sequence identity to the mature polypeptide of SEQ ID NO: 4 of at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9% or even 100%, and wherein the polypeptide has at least at least 85% of the protease activity of the mature polypeptide of SEQ ID NO: 4.

In a particular embodiment the invention relates to polypeptides having a sequence identity to the mature polypeptide of SEQ ID NO: 4 of at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9% or even 100%, and wherein the polypeptide has at least at least 90% of the protease activity of the mature polypeptide of SEQ ID NO: 4.

In a particular embodiment the invention relates to polypeptides having a sequence identity to the mature polypeptide of SEQ ID NO: 4 of at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9% or even 100%, and wherein the polypeptide has at least at least 95% of the protease activity of the mature polypeptide of SEQ ID NO: 4.

In a particular embodiment the invention relates to polypeptides having a sequence identity to the mature polypeptide of SEQ ID NO: 4 of at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9% or even 100%, and wherein the polypeptide has at least at least 100% of the protease activity of the mature polypeptide of SEQ ID NO: 4.

"Protease activity" can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of general protease substrates are casein, bovine serum albumin and haemoglobin. In the classical Anson and Mirsky method, denatured haemoglobin is used as substrate and after the assay incubation with the protease in question, the amount of trichloroacetic acid soluble haemoglobin is determined as a measurement of protease activity (Anson, M. L. and Mirsky, A. E., 1932, *J. Gen. Physiol.* 16: 59 and Anson, M. L., 1938, *J. Gen. Physiol.* 22: 79).

For the purpose of the present invention, protease activity was determined using assays which are described in "Materials and Methods", such as the Protazyme OL assay.

The term "metalloprotease" as used herein refers to a protease having one or more metal ions in the binding/active site.

The term "M4 Metalloprotease Family" or "M4 Metalloprotease" or "M4" as used herein means a polypeptide falling into the M4 metalloprotease family according to Rawlings et al., Biochem. J., 290, 205-218 (1993) and as further described in MEROPS—(Rawlings et al., MEROPS:

the peptidase database, Nucl Acids Res, 34 Database issue, D270-272, 2006). The M4 metalloproteases are neutral metalloproteases containing mainly endopeptidases. All peptidases in the family bind a single, catalytic zinc ion. M4 metalloprotease family members include the common HEXXH motif, where the histidine residues serve as zinc ligands and glutamate is an active site residue.

The M4 metalloprotease family includes, e.g., Neutrase® (classified as MEROPS subclass M04.014), Thermolysin, Bacillolysin, vibriolysin, pseudolysin, Msp peptidase, coccolysin, aureolysin, vimelysin, lambda toxin neutral peptidase B, PA peptidase (*Aeromonas*-type), griselysin, stearolysin, MprIII (*Alteromonas* sp. strain O-7), pap6 peptidase, neutral peptidase (*Thermoactinomyces*-type), ZmpA peptidase (*Burkholderia* sp.), zpx peptidase, PrtS peptidase (*Photorhabdus luminescens*), protealysin, ZmpB peptidase (*Burkholderia* sp.). The M4 metalloprotease family of polypeptides has been further characterized and presently includes, according to MEROPS, at least twenty-two subclasses for which a distinct MEROPS ID (i.e., an identifier of the formula M04.xxx) has been assigned, as well as non-peptidase homologues and unassigned peptidases.

In the *Streptomyces thermoalcalitolerans* metalloprotease of the present invention, H142 and H146 of the HEXXH motif together with E166 are the zinc ligands. Residue E143 of the HEXXH motif and H230 are the active site residues of the enzyme (numbering according to SEQ ID NO. 2). In the *Lysobacter capsici* metalloprotease of the present invention, H131 and H135 of the HEXXH motif together with E155 are the zinc ligands. Residue E132 of the HEXXH motif and H215 are the active site residues of the enzyme (numbering according to SEQ ID NO. 4). The *Streptomyces thermoalcalitolerans* metalloprotease appear to be of MEROPS subclass M4.017. The *Lysobacter capsici* metalloprotease appear to be of MEROPS subclass M4.003 (and EC 3.4.24.25).

The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample. A fermentation broth resulting from the fermentation of a recombinant host cell expressing the polypeptide of the invention will comprise the polypeptide in an isolated form.

The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form. This can be accomplished, for example, by preparing the variant or polypeptide by well-known recombinant methods or by classical purification methods.

The term "mature polypeptide" means a polypeptide in its final form following translation and any post-translational modifications, such as N-terminal processing, C-terminal truncation, glycosylation, phosphorylation, etc.

In one aspect, the mature polypeptide is amino acids 1 to 328 of SEQ ID NO: 2 based on the determination of the N-terminal sequence GTGRTLY. Further, amino acids −224 to −190 of SEQ ID NO: 2 are a signal peptide. Amino acids −189 to −1 of SEQ ID NO: 2 are a propeptide, based on the determination of the N-terminal and the signal sequence.

The term "mature polypeptide coding sequence" means a polynucleotide that encodes a mature polypeptide having protease activity. In one aspect, the mature polypeptide coding sequence is nucleotides 673 to 1656 of SEQ ID NO: 1 based on the experimental determination of the N-terminal sequence. Nucleotides 1 to 105 of SEQ ID NO: 1 encodes a signal peptide. Nucleotides 106 to 672 of SEQ ID NO: 1 encodes a propeptide.

In another aspect, the mature polypeptide is amino acids 1 to 290 of SEQ ID NO: 4. Further, amino acids −226 to −206 of SEQ ID NO: 4 are a signal peptide. Amino acids −205 to −1 of SEQ ID NO: 4 are a propeptide.

The term "mature polypeptide coding sequence" means a polynucleotide that encodes a mature polypeptide having protease activity. In one aspect, the mature polypeptide coding sequence is nucleotides 679 to 1548 of SEQ ID NO: 3 based on the experimental determination of the N-terminal sequence. Nucleotides 1 to 69 of SEQ ID NO: 3 encode a signal peptide. Nucleotides 70 to 678 of SEQ ID NO: 3 encode a propeptide.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C. The carrier material is finally washed three times each for 15 minutes using 2×SSC, 0.2% SDS at 60° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C. The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C. The relatedness between two amino acid sequences or between two nucleotide sequences is described by the parameter "sequence identity". For purposes of the present invention, the degree of identity between two amino acid sequences is determined using the Needleman-Wunsch algorithm (Needleman and Wunsch, 1970, $J.\ Mol.\ Biol.$ 48: 443-453) as implemented in the Needle program of the EMBOSS package (EMBOSS: The European Molecular Biology Open Software Suite, Rice et al., 2000, $Trends\ in\ Genetics$ 16: 276-277; available on the world wide web), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

(Identical Residues×100)/(Length of Alignment−
Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra; available on the world wide web), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of
Alignment−Total Number of Gaps in Alignment)

The term "fragment" means a polypeptide having one or more (several) amino acids deleted from the amino and/or carboxyl terminus of a mature polypeptide; wherein the fragment has protease activity.

The term "functional fragment of a polypeptide" or "functional fragment thereof" is used to describe a polypeptide which is derived from a longer polypeptide, e.g., a mature polypeptide, and which has been truncated either in the N-terminal region or the C-terminal region or in both regions to generate a fragment of the parent polypeptide. To be a functional polypeptide the fragment must maintain at least 20%, preferably at least 40%, more preferably at least 50%, more preferably at least 60%, more preferably at least 70%, more preferably at least 80%, even more preferably at least 90%, most preferably at least 95%, and even most preferably at least 100% of the protease activity of the full-length/mature polypeptide. An M4 metalloprotease may be truncated such that certain domain is removed to generate a functional fragment, which may be polypeptides where less than 200 amino acids have been removed from the mature M4 Metalloprotease, preferably less than 150 amino acids, more preferably less than 120, 100, 80, 60, 40, 30 amino acids, even more preferably less than 20 amino acids and most preferably less than 10 amino acids, such as 9, 8, 7, 6, 5, 4, 3, 2 or one amino acids have been removed from the mature polypeptide.

The term "subsequence" means a polynucleotide having one or more (several) nucleotides deleted from the 5' and/or 3' end of a mature polypeptide coding sequence; wherein the subsequence encodes a fragment having protease activity.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "variant" means a polypeptide having protease activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1, 2 or even 3 amino acids adjacent to an amino acid occupying a position.

The terms "cleaning compositions" and "cleaning formulations," refer to compositions that find use in the removal of undesired compounds from items to be cleaned, such as fabric, carpets, dishware including glassware, contact lenses, hard surfaces such as tiles, zincs, floors, and table surfaces, hair (shampoos), skin (soaps and creams), teeth (mouthwashes, toothpastes), etc. The terms encompasses any materials/compounds selected for the particular type of cleaning composition desired and the form of the product (e.g., liquid, gel, granule, or spray compositions), as long as the composition is compatible with the metalloprotease and other enzyme(s) used in the composition. The specific selection of cleaning composition materials is readily made by considering the surface, item or fabric to be cleaned, and the desired form of the composition for the cleaning conditions during use. These terms further refer to any composition that is suited for cleaning, bleaching, disinfecting, and/or sterilizing any object and/or surface. It is intended that the terms include, but are not limited to detergent composition (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dishwash detergents).

The term "detergent composition", includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types.

The terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. It is intended that in addition to the metalloprotease according to the invention, the term encompasses detergents that contains, e.g., surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "fabric" encompasses any textile material. Thus, it is intended that the term encompass garments, as well as fabrics, yarns, fibers, non-woven materials, natural materials, synthetic materials, and any other textile material.

The term "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers. The term, "textile materials" is a general term for fibers, yarn intermediates, yarn, fabrics, and products made from fabrics (e.g., garments and other articles).

The term "non-fabric detergent compositions" include non-textile surface detergent compositions, including but not limited to dishwashing detergent compositions, oral detergent compositions, denture detergent compositions, and personal cleansing compositions.

The term "effective amount of enzyme" refers to the quantity of enzyme necessary to achieve the enzymatic activity required in the specific application, e.g., in a defined detergent composition. Such effective amounts are readily ascertained by one of ordinary skill in the art and are based on many factors, such as the particular enzyme used, the cleaning application, the specific composition of the detergent composition, and whether a liquid or dry (e.g., granular, bar) composition is required, and the like. The term "effective amount" of a metalloprotease refers to the quantity of metalloprotease described hereinbefore that achieves a desired level of enzymatic activity, e.g., in a defined detergent composition.

The term "wash performance" of an enzyme refers to the contribution of an enzyme to washing that provides additional cleaning performance to the detergent without the addition of the enzyme to the composition. Wash performance is compared under relevant washing conditions. Wash performance of enzymes is conveniently measured by their ability to remove certain representative stains under appropriate test conditions. In these test systems, other relevant factors, such as detergent composition, detergent concentration, water hardness, washing mechanics, time, pH, and/or temperature, can be controlled in such a way that conditions typical for household application in a certain market segment are imitated.

The term "water hardness" or "degree of hardness" or "dH" or "° dH" as used herein refers to German degrees of hardness. One degree is defined as 10 milligrams of calcium oxide per litre of water.

The term "relevant washing conditions" is used herein to indicate the conditions, particularly washing temperature, time, washing mechanics, detergent concentration, type of detergent and water hardness, actually used in households in a detergent market segment.

The term "improved property" is used to indicate that a better end result is obtained in a property compared to the same process performed without the enzyme. Exemplary properties which are preferably improved in the processes of the present invention include wash performance, enzyme stability, enzyme activity and substrate specificity.

The term "improved wash performance" is used to indicate that a better end result is obtained in stain removal from items washed (e.g., fabrics or dishware and/or cutlery) under relevant washing conditions as compared to no enzyme or to a reference enzyme, or that less enzyme, on weight basis, is needed to obtain the same end result relative to no enzyme or to a reference enzyme. Improved wash performance could in this context also be that the same effect, e.g., stain removal effect is obtained in shorter wash time, e.g., the enzymes provide their effect more quickly under the tested conditions.

The term "enzyme detergency" or "detergency" or "detergency effect" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process an effect that also is termed anti-redeposition, restoring fully or partly the whiteness of textiles, which originally were white but after repeated use and wash have obtained a greyish or yellowish appearance an effect that also is termed whitening. Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric an effect that is also termed dye transfer inhibition or anti-back staining, removal of protruding or broken fibers from a fabric surface to decrease pilling tendencies or remove already existing pills or fuzz an effect that also is termed anti-pilling, improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching component such as hydrogen peroxide or other peroxides.

The term "anti-redeposition" as used herein describes the reduction or prevention of redeposition of soils dissolved or suspended in the wash liquor onto the cleaned objects. Redeposition may be seen after one or multiple washing cycles (e.g., as a greying, yellowing or other discolorations).

The term "adjunct materials" means any liquid, solid or gaseous material selected for the particular type of detergent composition desired and the form of the product (e.g., liquid, granule, powder, bar, paste, spray, tablet, gel, or foam composition), which materials are also preferably compatible with the metalloprotease enzyme used in the composition. In some embodiments, granular compositions are in "compact" form, while in other embodiments, the liquid compositions are in a "concentrated" form.

The term "stain removing enzyme" as used herein, describes an enzyme that aids the removal of a stain or soil from a fabric or a hard surface. Stain removing enzymes act on specific substrates, e.g., protease on protein, amylase on starch, lipase and cutinase on lipids (fats and oils), pectinase on pectin and hemicellulases on hemicellulose. Stains are often depositions of complex mixtures of different components which either results in a local discolouration of the material by itself or which leaves a sticky surface on the object which may attract soils dissolved in the washing liquor thereby resulting in discolouration of the stained area. When an enzyme acts on its specific substrate present in a stain the enzyme degrades or partially degrades its substrate thereby aiding the removal of soils and stain components associated with the substrate during the washing process. For example, when a protease acts on a grass stain it degrades the protein components in the grass and allows the green/brown colour to be released during washing.

The term "reduced amount" means in this context that the amount of the component is smaller than the amount which would be used in a reference process under otherwise the same conditions. In a preferred embodiment the amount is reduced by, e.g., at least 5%, such as at least 10%, at least 15%, at least 20% or as otherwise herein described.

The term "low detergent concentration" system includes detergents were less than about 800 ppm of detergent components is present in the wash water. Asian, e.g., Japanese detergents are typically considered low detergent concentration systems.

The term "medium detergent concentration" system includes detergents wherein between about 800 ppm and about 2000 ppm of detergent components is present in the wash water. North American detergents are generally considered to be medium detergent concentration systems.

The term "high detergent concentration" system includes detergents wherein greater than about 2000 ppm of detergent components is present in the wash water. European detergents are generally considered to be high detergent concentration systems.

Polypeptides Having Protease Activity

In an embodiment, the present invention relates to isolated polypeptides having a sequence identity to the mature polypeptide of SEQ ID NO: 2, or the mature polypeptide of SEQ ID NO: 4 of at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity or at least 100% sequence identity, which have protease activity. In one aspect, the polypeptides differ by no more than 10 amino acids, e.g., 1, 2, 3, 4, 5, 6, 7, 8, or 9, from the mature polypeptide of SEQ ID NO: 2.

In a particular embodiment the invention relates to polypeptides having a sequence identity to the mature polypeptide of SEQ ID NO: 2, or the mature polypeptide of SEQ ID NO: 4 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the mature polypeptide of SEQ ID NO: 2.

In a particular embodiment the invention relates to polypeptides having a sequence identity to the mature polypeptide of SEQ ID NO: 2 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the mature polypeptide of SEQ ID NO: 2.

In a particular embodiment the invention relates to polypeptides having a sequence identity to the mature polypeptide of SEQ ID NO: 2 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 2.

In a particular embodiment the invention relates to polypeptides having a sequence identity to the mature polypeptide of SEQ ID NO: 2 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the mature polypeptide of SEQ ID NO: 2.

In a particular embodiment the invention relates to polypeptides having a sequence identity to the mature polypeptide of SEQ ID NO: 2 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the mature polypeptide of SEQ ID NO: 2.

In a particular embodiment the invention relates to polypeptides having a sequence identity to the mature polypeptide of SEQ ID NO: 2 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the mature polypeptide of SEQ ID NO: 2.

In a particular embodiment the invention relates to polypeptides having a sequence identity to the mature polypeptide of SEQ ID NO: 2 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the mature polypeptide of SEQ ID NO: 2.

In an embodiment, the present invention relates to isolated polypeptides having a sequence identity to the mature polypeptide of SEQ ID NO: 2, or the mature polypeptide of SEQ ID NO: 4 of at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity or at least 100% sequence identity, which have protease activity. In one aspect, the polypeptides differ by no more than 10 amino acids, e.g., 1, 2, 3, 4, 5, 6, 7, 8, or 9, from the mature polypeptide of SEQ ID NO: 2.

In a particular embodiment the invention relates to polypeptides having a sequence identity to the mature polypeptide of SEQ ID NO: 4, or the mature polypeptide of SEQ ID NO: 4 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the mature polypeptide of SEQ ID NO: 4.

In a particular embodiment the invention relates to polypeptides having a sequence identity to the mature polypeptide of SEQ ID NO: 4 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the mature polypeptide of SEQ ID NO: 4.

In a particular embodiment the invention relates to polypeptides having a sequence identity to the mature polypeptide of SEQ ID NO: 4 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 4.

In a particular embodiment the invention relates to polypeptides having a sequence identity to the mature polypeptide of SEQ ID NO: 4 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the mature polypeptide of SEQ ID NO: 4.

In a particular embodiment the invention relates to polypeptides having a sequence identity to the mature polypeptide of SEQ ID NO: 4 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the mature polypeptide of SEQ ID NO: 4.

In a particular embodiment the invention relates to polypeptides having a sequence identity to the mature polypeptide of SEQ ID NO: 4 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the mature polypeptide of SEQ ID NO: 4.

In a particular embodiment the invention relates to polypeptides having a sequence identity to the mature polypeptide of SEQ ID NO: 4 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the mature polypeptide of SEQ ID NO: 4.

In a preferred embodiment the present invention relates to isolated polypeptides having protease activity selected from the group consisting of:

(a) a polypeptide having at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity or at least 100% sequence identity to the mature polypeptide of SEQ ID NO: 2, or the mature polypeptide of SEQ ID NO: 4;

(b) a polypeptide encoded by a polynucleotide that hybridizes under medium stringency conditions with (i) the mature polypeptide coding sequence of SEQ ID NO: 1 or of SEQ ID NO: 3 or (ii) the full-length complementary strand of (i);

(c) a polypeptide encoded by a polynucleotide having at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity or at least 100% sequence identity to the mature polypeptide coding sequence of SEQ ID NO: 1 or of SEQ ID NO: 3;

(d) a variant comprising a substitution, deletion, and/or insertion of one or more (e.g. several) amino acids of the mature polypeptide of SEQ ID NO: 2, or the mature polypeptide of SEQ ID NO: 4; and (e) a fragment of a polypeptide of (a), (b), (c), or (d) that has protease activity.

The present invention relates to isolated polypeptides having a sequence identity to the mature polypeptide of SEQ ID NO: 2, or the mature polypeptide of SEQ ID NO: 4 of at least 85%, at least 86%, at least 87%, at least 88%, at least 89% sequence identity, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than ten amino acids, e.g., by five amino acids, by four amino acids, by three amino acids, by two amino acids, and by one amino acid from the mature polypeptide of SEQ ID NO: 2, or the mature polypeptide of SEQ ID NO: 4.

A polypeptide of the present invention preferably comprises or consists of the amino acid sequence of SEQ ID NO: 2 or of SEQ ID NO: 4, or an allelic variant thereof; or is a fragment thereof having protease activity. In another aspect, the polypeptide comprises or consists of the mature polypeptide of SEQ ID NO: 2, or the mature polypeptide of SEQ ID NO: 4 or an allelic variant thereof; or is a fragment thereof having protease activity. In one preferred aspect, the polypeptide comprises or consists of amino acids 1 to 328 of SEQ ID NO: 2. In another preferred aspect, the polypeptide comprises or consists of amino acids 1 to 290 of SEQ ID NO: 4.

The present invention also relates to isolated polypeptides having protease activity that are encoded by polynucleotides that hybridize under very low stringency conditions, low stringency conditions, medium stringency conditions, medium-high stringency conditions, high stringency conditions, or very high stringency conditions with (i) the mature polypeptide coding sequence of SEQ ID NO: 1 or of SEQ ID NO: 3, (ii) the genomic DNA sequence encoding the mature polypeptide coding sequence of SEQ ID NO: 1 or of SEQ ID NO: 3, or (iii) the full-length complementary strand of (i) or (ii) (J. Sambrook, E. F. Fritsch, and T. Maniatis, 1989, *Molecular Cloning, A Laboratory Manual*, 2d edition, Cold Spring Harbor, New York).

The polynucleotide of SEQ ID NO: 1 or of SEQ ID NO: 3 or a subsequence thereof, as well as the amino acid sequence of SEQ ID NO: 2 or a fragment thereof, may be used to design nucleic acid probes to identify and clone DNA encoding polypeptides having protease activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having protease activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or a subsequence thereof, the carrier material is preferably used in a Southern blot.

For purposes of the present invention, hybridization indicates that the polynucleotide hybridizes to a labeled nucleic acid probe corresponding to the mature polypeptide coding sequence of SEQ ID NO: 1 or of SEQ ID NO: 3; the genomic DNA sequence comprising the mature polypeptide coding sequence of SEQ ID NO: 1 or of SEQ ID NO: 3; its full-length complementary strand; or a subsequence thereof; under very low to very high stringency conditions. Molecules to which the nucleic acid probe hybridizes under these conditions can be detected using, for example, X-ray film.

In one aspect, the nucleic acid probe is the mature polypeptide coding sequence of SEQ ID NO: 1 or of SEQ ID NO: 3. In another aspect, the nucleic acid probe is nucleotides 574 to 2040 of SEQ ID NO: 1 or of SEQ ID NO: 3. In another aspect, the nucleic acid probe is a polynucleotide that encodes the polypeptide of SEQ ID NO: 2 or a fragment thereof. In another preferred aspect, the nucleic acid probe is SEQ ID NO: 1 or SEQ ID NO: 3.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The present invention relates to isolated polypeptides having protease activity encoded by polynucleotides having a sequence identity to the mature polypeptide coding sequence of SEQ ID NO: 1 or SEQ ID NO: 3 of at least at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity or at least 100%.

The present invention also relates to variants comprising a substitution, deletion, and/or insertion of one or more (or several) amino acids of the mature polypeptide of SEQ ID NO: 2, or the mature polypeptide of SEQ ID NO: 4, or a homologous sequence thereof. Preferably the variant has at least 85% sequence identity, at least 86% sequence identity, at least 87% sequence identity, at least 88% sequence identity, at least 89% sequence identity, at least 90% sequence identity, at least 91% sequence identity, at least 92% sequence, at least 93% sequence identity, at least 94% sequence identity, at least 95% sequence identity, at least 96% sequence identity, at least 97% sequence identity, at least 98% sequence identity, at least 99% sequence identity %, but less than 100% identity to the mature polypeptide of SEQ ID NO: 2, or the mature polypeptide of SEQ ID NO: 4.

Substantially homologous polypeptides of the sequences described above are characterized as having one or more (several) amino acid substitutions, deletions, and/or insertions in the mature polypeptide. Preferably, amino acid changes are of a minor nature, that is conservative amino acid substitutions or insertions that do not significantly affect the folding and/or activity of the protein; small deletions, typically of one to about nine amino acids, such as one, two, three, four, five, six, seven, eight or nine amino acids; preferably from one to about 15 amino acids, such as 10, 11, 12, 13, 14 or 15 amino acids; and most preferably from one to about 30 amino acids, such as 16, 17, 18, 19, 20, 21, 22, 23, 24, 25, 26, 27, 28, 29 or 30 amino acids; small amino- or carboxyl-terminal extensions, such as an amino-terminal methionine residue; a small linker peptide of up to about five to ten residues, preferably from 10 to 15 residues and most preferably from 20 to 25 residues, or a small extension that facilitates purification by changing net charge or another function, such as a poly-histidine tag, an antigenic epitope, protein A, a carbohydrate binding module or a another binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant variant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide, such as e.g. the well-known metalloproteinase Thermolysin. The catalytic residues may thus be determined by alignment with known M4 metalloprotease where it has been found that the catalytic residues are conserved in all such proteases.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The total number of amino acid substitutions, deletions and/or insertions of the mature polypeptide of SEQ ID NO: 2, or the mature polypeptide of SEQ ID NO: 4 are not more than 10, e.g., 1, 2, 3, 4, 5, 6, 7, 8 or 9.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

The polypeptide may be hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of M4 Metalloproteases

A M4 Metalloprotease of the present invention may be obtained from a microorganism. For purposes of the present invention, the term "obtained from" as used herein in connection with a given source shall mean that the polypeptide encoded by a nucleotide sequence is produced by the source in which it is naturally present or by a strain in which the nucleotide sequence from the source has been inserted. In a preferred aspect, the polypeptide obtained from a given source is secreted extracellularly.

A polypeptide of the present invention may be a bacterial polypeptide having metalloprotease activity.

In one aspect the polypeptide is a polypeptide derived from *Streptomyces*, preferably from *Streptomyces thermoalcalitolerans*, e.g., the polypeptide in SEQ ID NO: 2.

In another aspect the polypeptide is a polypeptide derived from *Lysobacter*, preferably from *Lysobacter capsici*, e.g., the polypeptide in SEQ ID NO: 4.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the abovementioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected e.g. with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Streptomyces*, e.g. from a strain of *Streptomyces thermoalcalitolerans*, or a related organism and thus, for example, may be an allelic or species variant of the polypeptide encoding region of the polynucleotide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3- phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, Bacillus, Clostridium, Enterococcus, Geobacillus, Lactobacillus, Lactococcus, Oceanobacillus, Staphylococcus, Streptococcus, and Streptomyces. Gram-negative bacteria include, but are not limited to, Campylobacter, E. coli, Flavobacterium, Fusobacterium, Helicobacter, Ilyobacter, Neisseria, Pseudomonas, Salmonella, and Ureaplasma.

The bacterial host cell may be any Bacillus cell including, but not limited to, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, and Bacillus thuringiensis cells.

The bacterial host cell may also be any Streptococcus cell including, but not limited to, Streptococcus equisimilis, Streptococcus pyogenes, Streptococcus uberis, and Streptococcus equi subsp. Zooepidemicus cells.

The bacterial host cell may also be any Streptomyces cell including, but not limited to, Streptomyces achromogenes, Streptomyces avermitilis, Streptomyces coelicolor, Streptomyces griseus, and Streptomyces lividans cells.

The introduction of DNA into a Bacillus cell may be effected by protoplast transformation (see, e.g., Chang and Cohen, 1979, Mol. Gen. Genet. 168: 111-115), competent cell transformation (see, e.g., Young and Spizizen, 1961, J. Bacteriol. 81: 823-829, or Dubnau and Davidoff-Abelson, 1971, J. Mol. Biol. 56: 209-221), electroporation (see, e.g., Shigekawa and Dower, 1988, Biotechniques 6: 742-751), or conjugation (see, e.g., Koehler and Thorne, 1987, J. Bacteriol. 169: 5271-5278). The introduction of DNA into an E. coli cell may be effected by protoplast transformation (see, e.g., Hanahan, 1983, J. Mol. Biol. 166: 557-580) or electroporation (see, e.g., Dower et al., 1988, Nucleic Acids Res. 16: 6127-6145). The introduction of DNA into a Streptomyces cell may be effected by protoplast transformation, electroporation (see, e.g., Gong et al., 2004, Folia Microbiol. (Praha) 49: 399-405), conjugation (see, e.g., Mazodier et al., 1989, J. Bacteriol. 171: 3583-3585), or transduction (see, e.g., Burke et al., 2001, Proc. Natl. Acad. Sci. USA 98: 6289-6294). The introduction of DNA into a Pseudomonas cell may be effected by electroporation (see, e.g., Choi et al., 2006, J. Microbiol. Methods 64: 391-397) or conjugation (see, e.g., Pinedo and Smets, 2005, Appl. Environ. Microbiol. 71: 51-57). The introduction of DNA into a Streptococcus cell may be effected by natural competence (see, e.g., Perry and Kuramitsu, 1981, Infect. Immun. 32: 1295-1297), protoplast transformation (see, e.g., Catt and Jollick, 1991, Microbios 68: 189-207), electroporation (see, e.g., Buckley et al., 1999, Appl. Environ. Microbiol. 65: 3800-3804), or conjugation (see, e.g., Clewell, 1981, Microbiol. Rev. 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a Candida, Hansenula, Kluyveromyces, Pichia, Saccharomyces, Schizosaccharomyces, or Yarrowia cell, such as a Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, or Yarrowia lipolytica cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

The filamentous fungal host cell may be an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

For example, the filamentous fungal host cell may be an Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor,

*Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

The host cell may be a plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a *Streptomyces* cell. In a more preferred aspect, the cell is a *Streptomyces thermoalcalitolerans* cell.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fedbatch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides with protease activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Signal Peptide and Propeptide

The present invention also relates to an isolated polynucleotide encoding a signal peptide comprising or consisting of amino acids −224 to −190 of SEQ ID NO: 2. The present invention also relates to an isolated polynucleotide encoding a propeptide comprising or consisting of amino acids −189 to −1 of SEQ ID NO: 2. The present invention also relates to an isolated polynucleotide encoding the signal peptide and the propeptide. The polynucleotides may further comprise a gene encoding a protein, which is operably linked to the signal peptide and/or propeptide. The protein is preferably foreign to the signal peptide and/or propeptide. In one aspect, the polynucleotide encoding the signal peptide is nucleotides 1-105 of SEQ ID NO: 1. In another aspect, the polynucleotide encoding the propeptide is nucleotides 106-672 of SEQ ID NO: 1.

The present invention further relates to an isolated polynucleotide encoding a signal peptide comprising or consisting of amino acids −226 to −206 of SEQ ID NO: 4. The present invention also relates to an isolated polynucleotide encoding a propeptide comprising or consisting of amino acids −205 to −1 of SEQ ID NO: 4. The present invention also relates to an isolated polynucleotide encoding the signal peptide and the propeptide. The polynucleotides may further comprise a gene encoding a protein, which is operably linked to the signal peptide and/or propeptide. The protein is preferably foreign to the signal peptide and/or propeptide. In one aspect, the polynucleotide encoding the signal peptide is nucleotides 1 to 69 of SEQ ID NO: 3. In another aspect, the polynucleotide encoding the propeptide is nucleotides 70 to 678 of SEQ ID NO: 3.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, betagalactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

Compositions

The present invention also relates to compositions comprising a metalloprotease of the invention. Preferably, the compositions are enriched in a metalloprotease of the invention. The term "enriched" indicates that the protease activity of the composition has been increased.

In one embodiment, the present invention relates to compositions in particular to cleaning compositions and/or detergent compositions comprising a metalloprotease of the invention and a suitable carrier and/or excipient.

The present invention also relates to compositions comprising an isolated polypeptide having protease activity selected from the group consisting of: a) a polypeptide having at least 60% sequence identity, at least 65% sequence identity, at least 70% sequence identity, at least 75% sequence identity, at least 80% sequence identity, at least 85% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity or even 100% sequence identity to the mature polypeptide of SEQ ID NO: 2, or the mature polypeptide of SEQ ID NO: 4; b) a polypeptide encoded by a polynucleotide that hybridizes under medium stringency conditions with (i) the mature polypeptide coding sequence of SEQ ID NO: 1 or SEQ ID NO: 3 or (ii) the full-length complementary strand of (i); c) a polypeptide encoded by a polynucleotide having at least 60% sequence identity, at least 65% sequence identity, at least 70% sequence identity, at least 75% sequence identity, at least 80% sequence identity, at least 85% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity or even 100% sequence identity to the mature polypeptide coding sequence of SEQ ID NO: 1 or SEQ ID NO: 3; e) a variant comprising a substitution, deletion, and/or insertion of one or more (e.g. several) amino acids of the mature polypeptide of SEQ ID NO: 2, or the mature polypeptide of SEQ ID NO: 4; and f) a fragment of a polypeptide of (a), (b), (c), or (d) that has protease activity.

In one embodiment the compositions of the invention comprises an isolated polypeptide having protease activity and having at least 60% sequence identity to the mature polypeptide of SEQ ID NO: 2, or the mature polypeptide of SEQ ID NO: 4.

In one embodiment the compositions of the invention comprises an isolated polypeptide having protease activity and having at least 65% sequence identity to the mature polypeptide of SEQ ID NO: 2, or the mature polypeptide of SEQ ID NO: 4.

In one embodiment the compositions of the invention comprises an isolated polypeptide having protease activity and having at least 70% sequence identity to the mature polypeptide of SEQ ID NO: 2, or the mature polypeptide of SEQ ID NO: 4.

In one embodiment the compositions of the invention comprises an isolated polypeptide having protease activity and having at least 75% sequence identity to the mature polypeptide of SEQ ID NO: 2, or the mature polypeptide of SEQ ID NO: 4.

In one embodiment the compositions of the invention comprises an isolated polypeptide having protease activity and having at least 80% sequence identity to the mature polypeptide of SEQ ID NO: 2, or the mature polypeptide of SEQ ID NO: 4.

In one embodiment the compositions of the invention comprises an isolated polypeptide having protease activity and having at least 85% sequence identity to the mature polypeptide of SEQ ID NO: 2, or the mature polypeptide of SEQ ID NO: 4.

In one embodiment the compositions of the invention comprises an isolated polypeptide having protease activity and having at least 90% sequence identity to the mature polypeptide of SEQ ID NO: 2, or the mature polypeptide of SEQ ID NO: 4.

In one embodiment the compositions of the invention comprises an isolated polypeptide having protease activity and having at least 91% sequence identity to the mature polypeptide of SEQ ID NO: 2, or the mature polypeptide of SEQ ID NO: 4.

In one embodiment the compositions of the invention comprises an isolated polypeptide having protease activity and having at least 92% sequence identity to the mature polypeptide of SEQ ID NO: 2, or the mature polypeptide of SEQ ID NO: 4.

In one embodiment the compositions of the invention comprises an isolated polypeptide having protease activity and having at least 93% sequence identity to the mature polypeptide of SEQ ID NO: 2, or the mature polypeptide of SEQ ID NO: 4.

In one embodiment the compositions of the invention comprises an isolated polypeptide having protease activity and having at least 94% sequence identity to the mature polypeptide of SEQ ID NO: 2, or the mature polypeptide of SEQ ID NO: 4.

In one embodiment the compositions of the invention comprises an isolated polypeptide having protease activity and having at least 95% sequence identity to the mature polypeptide of SEQ ID NO: 2, or the mature polypeptide of SEQ ID NO: 4.

In one embodiment the compositions of the invention comprises an isolated polypeptide having protease activity and having at least 96% sequence identity to the mature polypeptide of SEQ ID NO: 2, or the mature polypeptide of SEQ ID NO: 4.

In one embodiment the compositions of the invention comprises an isolated polypeptide having protease activity and having at least 97% sequence identity to the mature polypeptide of SEQ ID NO: 2, or the mature polypeptide of SEQ ID NO: 4.

In one embodiment the compositions of the invention comprises an isolated polypeptide having protease activity and having at least 98% sequence identity to the mature polypeptide of SEQ ID NO: 2, or the mature polypeptide of SEQ ID NO: 4.

In one embodiment the compositions of the invention comprises an isolated polypeptide having protease activity and having at least 99% sequence identity to the mature polypeptide of SEQ ID NO: 2, or the mature polypeptide of SEQ ID NO: 4.

In one embodiment the compositions of the invention comprises an isolated polypeptide having protease activity and having 100% sequence identity to the mature polypeptide of SEQ ID NO: 2, or the mature polypeptide of SEQ ID NO: 4.

In one embodiment, the present invention relates to compositions in particular to cleaning compositions and/or detergent compositions comprising a metalloprotease of the invention and a suitable carrier and/or excipient.

In one embodiment, the detergent composition may be adapted for specific uses such as laundry, in particular household laundry, dish washing or hard surface cleaning.

The detergent compositions of the invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. The detergent compositions of the invention may find use in hard surface cleaning, automatic dishwashing applications, as well as cosmetic applications such as dentures, teeth, hair and skin.

In a preferred embodiment, the detergent compositions comprise one or more conventional carrier(s) and/or excipient(s) such as those exemplified below.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

Unless otherwise noted, all component or composition levels provided herein are made in reference to the active level of that component or composition, and are exclusive of impurities, for example, residual solvents or by-products, which may be present in commercially available sources.

The metalloprotease of the invention is normally incorporated in the detergent composition at a level of from 0.000001% to 2% of enzyme protein by weight of the composition, preferably at a level of from 0.00001% to 1% of enzyme protein by weight of the composition, more preferably at a level of from 0.0001% to 0.75% of enzyme protein by weight of the composition, even more preferably at a level of from 0.001% to 0.5% of enzyme protein by weight of the composition.

Furthermore, the metalloprotease of the invention is normally incorporated in the detergent composition in such amounts that their concentration in the wash water is at a level of from 0.0000001% to 1% enzyme protein, preferably at a level of from 0.000005% to 0.01% of enzyme protein, more preferably at a level of from 0.000001% to 0.005% of enzyme protein, even more preferably at a level of from 0.00001% to 0.001% of enzyme protein in wash water.

As is well known, the amount of enzyme will also vary according to the particular application and/or as a result of the other components included in the compositions.

A composition for use in automatic dish wash (ADW), for example, may include 0.001%50%, such as 0.01%-25%, such as 0.02%-20%, such as 0.1-15% of enzyme protein by weight of the composition.

A composition for use in laundry granulation, for example, may include 0.0001%-50%, such as 0.001%-20%, such as 0.01%-15%, such as 0.05%-10% of enzyme protein by weight of the composition.

A composition for use in laundry liquid, for example, may include 0.0001%-10%, such as 0.001-7%, such as 0.1%-5% of enzyme protein by weight of the composition.

In some preferred embodiments, the detergent compositions provided herein are typically formulated such that, during use in aqueous cleaning operations, the wash water has a pH of from about 5.0 to about 11.5, or in alternative embodiments, even from about 6.0 to about 10.5, such as from about 5 to about 11, from about 5 to about 10, from about 5 to about 9, from about 5 to about 8, from about 5 to about 7, from about 6 to about 11, from about 6 to about 10, from about 6 to about 9, from about 6 to about 8, from about 6 to about 7, from about 7 to about 11, from about 7 to about 11, from about 8 to about 11, from about 9 to about 11, from about 9.5 to about 11, from about 7 to about 9, or from about 7 to about 8. In some preferred embodiments, granular or liquid laundry products are formulated such that the wash water has a pH from about 5.5 to about 8. Techniques for controlling pH at recommended usage levels include the use of buffers, alkalis, acids, etc., and are well known to those skilled in the art.

Enzyme components weights are based on total protein. All percentages and ratios are calculated by weight unless otherwise indicated. All percentages and ratios are calculated based on the total composition unless otherwise indicated. In the exemplified detergent composition, the enzymes levels are expressed by pure enzyme by weight of the total composition and unless otherwise specified, the detergent ingredients are expressed by weight of the total composition.

The enzymes of the present invention also find use in detergent additive products. A detergent additive product comprising a metalloprotease of the invention is ideally suited for inclusion in a wash process when, e.g., temperature is low, such as at temperatures about 40° C. or below, the pH is between 6 and 8 and the washing time short, e.g., below 30 min.

The detergent additive product may be a metalloprotease of the invention and preferably an additional enzyme. In one embodiment, the additive is packaged in dosage form for addition to a cleaning process. The single dosage may comprise a pill, tablet, gelcap or other single dosage unit including powders and/or liquids. In some embodiments, filler and/or carrier material(s) are included, suitable filler or carrier materials include, but are not limited to, various salts of sulfate, carbonate and silicate as well as talc, clay and the like. In some embodiments filler and/or carrier materials for liquid compositions include water and/or low molecular weight primary and secondary alcohols including polyols and diols. Examples of such alcohols include, but are not limited to, methanol, ethanol, propanol and isopropanol.

In one particularly preferred embodiment the metalloprotease according to the invention is employed in a granular composition or liquid, the metalloprotease may be in form of an encapsulated particle. In one embodiment, the encapsulating material is selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof.

The compositions according to the invention typically comprise one or more detergent ingredients. The term detergent compositions include articles and cleaning and treatment compositions. The term cleaning composition includes, unless otherwise indicated, tablet, granular or powder-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use. The composition can also be in unit dose packages, including those known in the art and those that are water soluble, water insoluble and/or water permeable.

In embodiments in which cleaning and/or detergent components may not be compatible with the metalloprotease of the present invention, suitable methods may be used for keeping the cleaning and/or detergent components and the metalloprotease separated (i.e., not in contact with each other) until combination of the two components is appropriate. Such separation methods include any suitable method known in the art (e.g., gelcaps, encapsulation, tablets, and physical separation e.g., by use of a water dissolvable pouch having one or more compartments).

As mentioned when the metalloprotease of the invention is employed as a component of a detergent composition (e.g., a laundry washing detergent composition, or a dishwashing detergent composition), it may, for example, be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are polyethyleneglycol (PEG) products with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), tin (II), cobalt (II), copper (II), nickel (II), and oxovanadium (IV)). The enzymes of the detergent compositions of the invention may also be stabilized using conventional stabilizing agents such as polyol, e.g., propylene glycol or glycerol, a sugar or sugar alcohol, lactic acid, and the composition may be formulated as described in, e.g., WO 92/19709 and WO 92/19708. The enzymes of the invention may also be stabilized by adding reversible enzyme inhibitors, e.g., of the protein type (as described in EP 544 777) or the boronic acid type. Other enzyme stabilizers are well known in the art, such as peptide aldehydes and protein hydrolysate, e.g. the metalloproteases according to the invention may be stabilized using peptide aldehydes or ketones such as described in WO2005/105826 and WO2009/118375.

Protected enzymes for inclusion in a detergent composition of the invention may be prepared, as mentioned above, according to the method disclosed in EP 238 216.

The composition may be augmented with one or more agents for preventing or removing the formation of the biofilm. These agents may include, but are not limited to, dispersants, surfactants, detergents, other enzymes, antimicrobials, and biocides.

The compositions of the invention may be applied in dosing elements to be used in an auto-dosing device. The dosing elements comprising the composition of the present invention can be placed into a delivery cartridge as that described in WO 2007/052004 and WO 2007/0833141. The dosing elements can have an elongated shape and set into an array forming a delivery cartridge which is the refill for an auto-dosing dispensing device as described in case WO 2007/051989. The delivery cartridge is to be placed in an auto-dosing delivery device, such as that described in WO 2008/053191.

Suitable disclosure of auto-dosing devices can be found in WO 2007/083139, WO 2007/051989, WO 2007/083141, WO 2007/083142 and EP2361964, Other Enzymes In one embodiment, a metalloprotease of the invention is combined with one or more enzymes, such as at least two enzymes, more preferred at least three, four or five enzymes. Preferably, the enzymes have different substrate specificity, e.g., proteolytic activity, amylolytic activity, lipolytic activity, hemicellulytic activity or pectolytic activity.

The detergent additive as well as the detergent composition may comprise one or more enzymes such as a protease, lipase, cutinase, an amylase, carbohydrase, cellulase, pectinase, mannanase, arabinase, galactanase, xylanase, oxidase, e.g., a laccase and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of animal, vegetable or microbial origin. Particularly suitable cellulases include those of bacterial or fungal origin. Chemically modified or protein engineered variants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 1999/001544.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases:

Suitable proteases include those of bacterial, fungal, plant, viral or animal origin e.g. microbial or vegetable origin. Microbial origin is preferred. Chemically modified or protein engineered variants are included. It may be an alkaline protease, such as a serine protease or another metalloprotease. A serine protease may for example be of the S1 family, such as trypsin, or the S8 family such as subtilisin. It may also be an additional metalloprotease, for example a thermolysin from e.g. family M4 or an other metalloprotease such as those from the M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin lentus, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellulomonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the protease variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases:

Suitable lipases include those of animal, vegetable or microbial origin. Particularly suitable lipases include those of bacterial or fungal origin. Chemically modified or protein engineered variants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipolase Ultra™' and Lipex™ (Novozymes A/S).

Amylases:

Suitable amylases which can be used together with metalloprotease of the invention may be an alpha-amylase or a glucoamylase and may be of bacterial or fungal origin. Chemically modified or protein engineered variants are included. Amylases include, for example, alpha-amylases obtained from *Bacillus*, e.g., a special strain of *Bacillus licheniformis*, described in more detail in GB 1,296,839. Suitable amylases include amylases having SEQ ID NO: 3 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO: 6 of WO 2006/

066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+I201F+ A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184. Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476. More preferred variants are those having a deletion in positions 181 and 182 or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476. Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264. Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one or more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+ G475K;

S125A+N128C+K178L+T182G+Y305R+G475K; or

S125A+N128C+T131I+T165I+K178L+T182G+Y305R+ G475K wherein the variants are C-terminally truncated and optionally further comprises a substitution at position 243 and/or a deletion at position 180 and/or position 181. Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one or more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions. Other examples are amylase variants such as those described in WO2011/098531, WO2013/001078 and WO2013/001087. Commercially available amylases are Duramyl™, Termamyl™, Fungamyl™, Stainzyme™, Stainzyme Plus™' Natalase™, Liquozyme X and BAN™ (from Novozymes A/S), and Rapidase™ Purastar™/Effectenz™, Powerase and Preferenz S100 (from Genencor International Inc./DuPont).

Peroxidases/Oxidases:

Suitable peroxidases/oxidases include those of plant, bacterial or fungal origin. Chemically modified or protein engineered variants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates as described above, liquids, in particular stabilized liquids, or slurries.

Surfactants

Typically, the detergent composition comprises (by weight of the composition) one or more surfactants in the range of 0% to 50%, preferably from 2% to 40%, more preferably from 5% to 35%, more preferably from 7% to 30%, most preferably from 10% to 25%, even most preferably from 15% to 20%. In a preferred embodiment the detergent is a liquid or powder detergent comprising less than 40%, preferably less than 30%, more preferably less than 25%, even more preferably less than 20% by weight of surfactant. The composition may comprise from 1% to 15%, preferably from 2% to 12%, 3% to 10%, most preferably from 4% to 8%, even most preferably from 4% to 6% of one or more surfactants. Preferred surfactants are anionic surfactants, non-ionic surfactants, cationic surfactants, zwitterionic surfactants, amphoteric surfactants, and mixtures thereof. Preferably, the major part of the surfactant is anionic. Suitable anionic surfactants are well known in the art and may comprise fatty acid carboxylates (soap), branched-chain, linear-chain and random chain alkyl sulfates or fatty alcohol sulfates or primary alcohol sulfates or alkyl benzenesulfonates such as LAS and LAB or phenylalknesulfonates or alkenyl sulfonates or alkenyl benzenesulfonates or alkyl ethoxysulfates or fatty alcohol ether sulfates or alpha-olefin sulfonate or dodecenyl/tetradecnyl-succinic acid. The anionic surfactants may be alkoxylated. The detergent composition may also comprise from 1 wt % to 10 wt % of non-ionic surfactant, preferably from 2 wt % to 8 wt %, more preferably from 3 wt % to 7 wt %, even more preferably less than 5 wt % of non-ionic surfactant. Suitable non-ionic surfactants are well known in the art and may comprise alcohol ethoxylates, and/or alkyl ethoxylates, and/or alkylphenol ethoxylates, and/or glucamides such as fatty acid N-glucosyl N-methyl amides, and/or alkyl polyglucosides and/or mono- or diethanolamides or fatty acid amides. The detergent composition may also comprise from 0 wt % to 10 wt % of cationic surfactant, preferably from 0.1 wt % to 8 wt %, more preferably from 0.5 wt % to 7 wt %, even more preferably less than 5 wt % of cationic surfactant. Suitable cationic surfactants are well known in the art and may comprise alkyl quaternary ammonium compounds, and/or alkyl pyridinium compounds and/or alkyl quaternary phosphonium compounds and/or alkyl ternary sulphonium compounds. The composition preferably comprises surfactant in an amount to provide from 100 ppm to 5,000 ppm surfactant in the wash liquor during the laundering process. The composition upon contact with water typically forms a wash liquor comprising from 0.5 g/l to 10 g/l detergent composition. Many suitable surface active compounds are available and fully described in the literature, for example, in "Surface-Active Agents and Detergents", Volumes I and 11, by Schwartz, Perry and Berch.

Builders

The main role of builder is to sequester divalent metal ions (such as calcium and magnesium ions) from the wash solution that would otherwise interact negatively with the surfactant system. Builders are also effective at removing metal ions and inorganic soils from the fabric surface, leading to improved removal of particulate and beverage stains. Builders are also a source of alkalinity and buffer the pH of the wash water to a level of 9.5 to 11. The buffering capacity is also termed reserve alkalinity, and should preferably be greater than 4.

The detergent compositions of the present invention may comprise one or more detergent builders or builder systems. Many suitable builder systems are described in the literature, for example in Powdered Detergents, Surfactant science series volume 71, Marcel Dekker, Inc. Builder may comprise from 0% to 60%, preferably from 5% to 45%, more preferably from 10% to 40%, most preferably from 15% to 35%, even more preferably from 20% to 30% builder by weight of the subject composition. The composition may comprise from 0% to 15%, preferably from 1% to 12%, 2% to 10%, most preferably from 3% to 8%, even most preferably from 4% to 6% of builder by weight of the subject composition.

Builders include, but are not limited to, the alkali metal, ammonium and alkanolammonium salts of polyphosphates (e.g., tripolyphosphate STPP), alkali metal silicates, alkaline earth and alkali metal carbonates, aluminosilicate builders (e.g., zeolite) and polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Ethanole amines (MEA, DEA, and TEA) may also contribute to the buffering capacity in liquid detergents.

Bleaches

The detergent compositions of the present invention may comprise one or more bleaching agents. In particular powdered detergents may comprise one or more bleaching agents. Suitable bleaching agents include other photobleaches, pre-formed peracids, sources of hydrogen peroxide, bleach activators, hydrogen peroxide, bleach catalysts and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) other photobleaches for example Vitamin K3;

(2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxone, and mixtures thereof. Suitable percarboxylic acids include hydrophobic and hydrophilic peracids having the formula R—(C=O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include inorganic salts such as alkali metal silicate, carbonate or borate salts or mixtures thereof, or organic materials such as water-soluble or dispersible polymers, waxes, oils or fatty soaps. Useful bleaching compositions are described in U.S. Pat. Nos. 5,576,282, and 6,306,812;

(4) bleach activators having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof; and (5) bleach catalysts that are capable of accepting an oxygen atom from peroxyacid and transferring the oxygen atom to an oxidizable substrate are described in WO 2008/007319. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof. The bleach catalyst will typically be comprised in the detergent composition at a level of from 0.0005% to 0.2%, from 0.001% to 0.1%, or even from 0.005% to 0.05% by weight.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Adjunct Materials

Dispersants—The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents—The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent—The detergent compositions of the present invention will preferably also contain additional components that may tint articles being cleaned, such as fluorescent whitening agent or optical brighteners. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate, 4,4'-bis-(2,4-dianilino-s-triazin-6-ylamino) stilbene-2,2'-disulphonate, 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate, 4,4'-bis-(2-anilino-4(1-methyl-2-hydroxy-ethylamino)-s-triazin-6-ylamino) stilbene-2,2'-disulphonate and, 2-(stilbyl-4"-naptho-1,2':4,5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate.

Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Fabric hueing agents—The detergent compositions of the present invention may also include fabric hueing agents such as dyes or pigments which when formulated in detergent compositions can deposit onto a fabric when said fabric is contacted with a wash liquor comprising said detergent compositions thus altering the tint of said fabric through absorption of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1 876 226. The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch.

Soil release polymers—The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series, volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523. Furthermore random graft co-polymers are suitable soil release polymers Suitable graft co-polymers are described in more detail in WO 2007/138054, WO 2006/108856 and WO 2006/113314. Other soil release polymers are substituted polysaccharide structures especially substituted cellulosic structures such as modified cellulose deriviatives such as those described in EP 1 867 808 or WO 2003/040279. Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents—The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, antiwrinkling agents, bactericides, binders, carriers, dyes, enzyme stabilizers, fabric softeners, fillers, foam regulators, hydrotropes, perfumes, pigments, sod suppressors, solvents, structurants for liquid detergents and/or structure elasticizing agents.

In one aspect the detergent is a compact fluid laundry detergent composition comprising: a) at least about 10%, preferably from 20 to 80% by weight of the composition, of surfactant selected from anionic surfactants, non ionic surfactants, soap and mixtures thereof; b) from about 1% to about 30%, preferably from 5 to 30%, by weight of the composition, of water; c) from about 1% to about 15%, preferably from 3 to 10% by weight of the composition, of non-amino functional solvent; and d) from about 5% to about 20%, by weight of the composition, of a performance additive selected from chelants, soil release polymers, enzymes and mixtures thereof; wherein the compact fluid laundry detergent composition comprises at least one of:
(i) the surfactant has a weight ratio of the anionic surfactant to the nonionic surfactant from about 1.5:1 to about 5:1, the surfactant comprises from about 15% to about 40%, by weight of the composition, of anionic surfactant and comprises from about 5% to about 40%, by weight of the composition, of the soap; (ii) from about 0.1% to about 10%, by weight of the composition, of a suds boosting agent selected from suds boosting polymers, cationic surfactants, zwitterionic surfactants, amine oxide surfactants, amphoteric surfactants, and mixtures thereof; and (ii) both (i) and (ii). All the ingredients are described in WO 2007/130562. Further polymers useful in detergent formulations are described in WO 2007/149806.

In another aspect the detergent is a compact granular (powdered) detergent comprising a) at least about 10%, preferably from 15 to 60% by weight of the composition, of surfactant selected from anionic surfactants, non-ionic surfactants, soap and mixtures thereof; b) from about 10 to 80% by weight of the composition, of a builder, preferably from 20% to 60% where the builder may be a mixture of builders selected from i) phosphate builder, preferably less than 20%, more preferably less than 10% even more preferably less than 5% of the total builder is a phosphate builder; ii) a zeolite builder, preferably less than 20%, more preferably less than 10% even more preferably less than 5% of the total builder is a zeolite builder; iii) citrate, preferably 0 to 5% of the total builder is a citrate builder; iv) polycarboxylate, preferably 0 to 5% of the total builder is a polycarboxylate builder v) carbonate, preferably 0 to 30% of the total builder is a carbonate builder and vi) sodium silicates, preferably 0 to 20% of the total builder is a sodium silicate builder; c) from about 0% to 25% by weight of the composition, of fillers such as sulphate salts, preferably from 1% to 15%, more preferably from 2% to 10%, more preferably from 3% to 5% by weight of the composition, of fillers; and d) from about 0.1% to 20% by weight of the composition, of enzymes, preferably from 1% to 15%, more preferably from 2% to 10% by weight of the composition, of enzymes.

Use of the M4 Metalloprotease in Detergents

The soils and stains that are important for detergent formulators are composed of many different substances, and a range of different enzymes, all with different substrate specificities have been developed for use in detergents both in relation to laundry and hard surface cleaning, such as dishwashing. These enzymes are considered to provide an enzyme detergency benefit, since they specifically improve stain removal in the cleaning process they are applied in as compared to the same process without enzymes. Stain removing enzymes that are known in the art include enzymes such as carbohydrases, amylases, proteases, lipases, cellulases, hemicellulases, xylanases, cutinases, and pectinase.

In one aspect, the present invention concerns the use of metalloprotease of the invention in detergent compositions and cleaning processes, such as laundry and hard surface cleaning. Thus, in one aspect, the present invention demonstrates the detergency effect of the metalloprotease of the invention on various stains and under various conditions. In a particular aspect of the invention the detergent composition and the use in cleaning process concerns the use of a metalloprotease of the invention together with at least one of the above mentioned stain removal enzymes, such as another protease, and in particular a serine protease.

In a preferred aspect of the present invention the metalloprotease of the invention useful according to the invention may be combined with at least two enzymes. These additional enzymes are described in details in the section "other enzymes", more preferred at least three, four or five enzymes. Preferably, the enzymes have different substrate specificity, e.g., carbolytic activity, proteolytic activity, amylolytic activity, lipolytic activity, hemicellulytic activity or pectolytic activity. The enzyme combination may for example be a metalloprotease of the invention with another stain removing enzyme, e.g., a metalloprotease of the invention and a protease, a metalloprotease of the invention and a serine protease, a metalloprotease of the invention and another metalloprotease, a metalloprotease of the invention and an amylase, a metalloprotease of the invention and a cellulase, a metalloprotease of the invention and a hemicellulase, a metalloprotease of the invention and a lipase, a metalloprotease of the invention and a cutinase, a metalloprotease of the invention and a pectinase or a metalloprotease of the invention and an anti-redeposition enzyme. More preferably, the metalloprotease of the invention is combined with at least two other stain removing enzymes, e.g., a metalloprotease of the invention, a lipase and an amylase; or a metalloprotease of the invention, a protease and an amylase; or a metalloprotease of the invention, a protease and a lipase; or a metalloprotease of the invention, a protease and a pectinase; or a metalloprotease of the invention, a protease and a cellulase; or a metalloprotease of the invention, a protease and a hemicellulase; or a metalloprotease of the invention, a protease and a cutinase; or a metalloprotease of the invention, an amylase and a pectinase; or a metalloprotease of the invention, an amylase and a cutinase; or a metalloprotease of the invention, an amylase and a cellulase; or a metalloprotease of the invention, an amylase and a hemicellulase; or a metalloprotease of the invention, a lipase and a pectinase; or a metalloprotease of the invention, a lipase and a cutinase; or a metalloprotease of the invention, a lipase and a cellulase; or a metalloprotease of the invention, a lipase and a hemicellulase. Even more preferably, a metalloprotease of the invention may be combined with at least three other stain removing enzymes, e.g., a metalloprotease of the invention, a protease, a lipase and an amylase; or a metalloprotease of the invention, a protease, an amylase and a pectinase; or a metalloprotease of the invention, a protease, an amylase and a cutinase; or a metalloprotease of the invention, a protease, an amylase and a cellulase; or a metalloprotease of the invention, a protease, an amylase and a hemicellulase; or a metalloprotease of the invention, an amylase, a lipase and a pectinase; or a metalloprotease of the invention, an amylase, a lipase and a cutinase; or a metalloprotease of the invention, an amylase, a lipase and a cellulase; or a metalloprotease of the invention, an amylase, a lipase and a hemicellulase; or a metalloprotease of the invention, a protease, a lipase and a pectinase; or a metalloprotease of the invention, a protease, a lipase and a cutinase; or a metalloprotease of the invention, a protease, a lipase and a cellulase; or a metalloprotease of the invention, a protease, a lipase and a hemicellulase. A metalloprotease according to the present invention may be combined with any of the enzymes selected from the non-exhaustive list comprising: carbohydrases, such as an amylase, a hemicellulase, a pectinase, a cellulase, a xanthanase or a pullulanase, a peptidase, a protease or a lipase.

In a preferred embodiment, a metalloprotease of the invention is combined with a serine protease, e.g., an S8 family protease such as Savinase®.

In another embodiment of the present invention, a metalloprotease of the invention useful according to the present invention may be combined with one or more other metalloproteases, such as another M4 metalloprotease, including Neutrase® or Thermolysin. Such combinations may further comprise combinations of the other detergent enzymes as outlined above.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one metalloprotease of the invention. The cleaning process or a textile care process can for example be carried out in a machine washing process or in a manual washing process. The washing solution can for example be an aqueous washing solution containing a detergent composition.

The fabrics and/or garments subjected to a washing, cleaning or textile care process of the present invention may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

The invention further concerns the use of metalloprotease of the invention in a proteinaceous stain removing processes. The proteinaceous stains may be stains such as food stains, e.g., baby food, sebum, cocoa, egg, blood, milk, ink, grass, or a combination hereof.

Typical detergent compositions includes various components in addition to the enzymes, these components have different effects, some components like the surfactants lower the surface tension in the detergent, which allows the stain being cleaned to be lifted and dispersed and then washed away, other components like bleach systems removes discolor often by oxidation and many bleaches also have strong bactericidal properties, and are used for disinfecting and sterilizing. Yet other components like builder and chelator softens, e.g., the wash water by removing the metal ions from the liquid.

In a particular embodiment, the invention concerns the use of a composition comprising a metalloprotease of the invention, wherein said enzyme composition further comprises at least one or more of the following a surfactant, a builder, a chelator or chelating agent, bleach system or bleach component in laundry or dish wash.

In a preferred embodiment of the invention the amount of a surfactant, a builder, a chelator or chelating agent, bleach system and/or bleach component are reduced compared to amount of surfactant, builder, chelator or chelating agent, bleach system and/or bleach component used without the added metalloprotease of the invention. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of metalloprotease of the invention, such as a conventional amount of such component. In one aspect, the metalloprotease of the invention is used in detergent compositions wherein said composition is free of at least one component which is a surfactant, a builder, a chelator or chelating agent, bleach system or bleach component and/or polymer.

Washing Method

The detergent compositions of the present invention are ideally suited for use in laundry applications. Accordingly, the present invention includes a method for laundering a fabric. The method comprises the steps of contacting a fabric to be laundered with a cleaning laundry solution comprising the detergent composition according to the invention. The fabric may comprise any fabric capable of being laundered in normal consumer use conditions. The solution preferably has a pH of from about 5.5 to about 8. The compositions may be employed at concentrations of from about 100 ppm, preferably 500 ppm to about 15,000 ppm in solution. The water temperatures typically range from about 5° C. to about 90° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8.

The metalloprotease from *Streptomyces thermoalcalitolerans* is active at alkaline pH as shown in Example 4. In a preferred embodiment the metalloprotease is used in a detergent composition for application in a washing method conducted at a pH of 7 to 11, a pH of 8 to 10, e.g., a pH of around 9.5.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

The present invention relates to a method of cleaning a fabric, a dishware or hard surface with a detergent composition comprising a metalloprotease of the invention.

A preferred embodiment concerns a method of cleaning, said method comprising the steps of: contacting an object with a cleaning composition comprising a metalloprotease of the invention under conditions suitable for cleaning said object. In a preferred embodiment the cleaning composition is a detergent composition and the process is a laundry or a dish wash process.

Still another embodiment relates to a method for removing stains from fabric which comprises contacting said a fabric with a composition comprising a metalloprotease of the invention under conditions suitable for cleaning said object.

In a preferred embodiment the compositions for use in the methods above further comprises at least one additional enzyme as set forth in the "other enzymes" section above, such as an enzyme selected from the group consisting of carbohydrases, peptidases, proteases, lipases, cellulase, xylanases or cutinases or a combination hereof. In yet another preferred embodiment the compositions comprises a reduced amount of at least one or more of the following components a surfactant, a builder, a chelator or chelating agent, bleach system or bleach component or a polymer.

Low Temperature Uses

One embodiment of the invention concerns a method of doing laundry, dish wash or industrial cleaning comprising contacting a surface to be cleaned with a metalloprotease of the invention, and wherein said laundry, dish wash, industrial or institutional cleaning is performed at a temperature of about 40° C. or below. One embodiment of the invention relates to the use of a metalloprotease in laundry, dish wash or a cleaning process wherein the temperature in laundry, dish wash, industrial cleaning is about 40° C. or below.

In another embodiment, the invention concerns the use of a metalloprotease according to the invention in a protein removing process, wherein the temperature in the protein removing process is about 40° C. or below.

The present invention also relates to the use in laundry, dish wash or industrial cleaning process of a metalloprotease having at least one improved property compared to a commercial metalloprotease such as Neutrase® and wherein the temperature in laundry, dish wash or cleaning process is performed at a temperature of about 40° C. or below.

In each of the above-identified methods and uses, the wash temperature is about 40° C. or below, such as about 39° C. or below, such as about 38° C. or below, such as about 37° C. or below, such as about 36° C. or below, such as about 35° C. or below, such as about 34° C. or below, such as about 33° C. or below, such as about 32° C. or below, such as about 31° C. or below, such as about 30° C. or below, such as about 29° C. or below, such as about 28° C. or below, such as about 27° C. or below, such as about 26° C. or below, such as about 25° C. or below, such as about 24° C. or below, such as about 23° C. or below, such as about 22° C. or below, such as about 21° C. or below, such as about 20° C. or below, such as about 19° C. or below, such as about 18° C. or below, such as about 17° C. or below, such as about 16° C. or below, such as about 15° C. or below, such as about 14° C. or below, such as about 13° C. or below, such as about 12° C. or below, such as about 11° C. or below, such as about 10° C. or below, such as about 9° C. or below, such as about 8° C. or below, such as about 7° C. or below, such as about 6° C. or below, such as about 5° C. or below, such as about 4° C. or below, such as about 3° C. or below, such as about 2° C. or below, such as about 1° C. or below.

In another preferred embodiment, the wash temperature is in the range of about 5-40° C., such as about 5-30° C., about 5-20° C., about 5-10° C., about 10-40° C., about 10-30° C., about 10-20° C., about 15-40° C., about 15-30° C., about 15-20° C., about 20-40° C., about 20-30° C., about 25-40° C., about 25-30° C., or about 30-40° C. In particular preferred embodiments the wash temperature is about 20° C., about 30° C., or about 40° C.

In particular embodiments, the low temperature washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, about 5.5 to about 9, preferably about 6 to about 8.5, and more preferably about 6 to about 8.

In particular embodiments, the low temperature washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

Use in Removing Egg Stains

Another particular embodiment of the invention concerns removal of egg stains. These types of stain are often very difficult to remove completely. Egg stains are particularly problematic in hard surface cleaning such as dish wash where the stains often remain on the plates and cutlery after washing. The metalloproteases of the invention are particularly suitable for removing egg stains.

Thus, the invention further concerns methods for removing egg stains from textiles, fabrics and/or hard surfaces like dishes and cutlery in particular from fabrics and textiles. A preferred aspect of the invention concerns a method of removing egg stains from textiles and/or fabrics comprising contacting a surface in need of removal of an egg stain with a metalloprotease of the invention. In one embodiment, the invention comprises a method of removing egg stains from textiles and/or fabrics comprising contacting a surface in need of removal of an egg stain with a detergent composition comprising a metalloprotease of the invention. The invention also concerns a method of removing egg stains comprising adding a metalloprotease of the invention to a laundry and/or washing process wherein said textiles and/or fabric comprises various egg stains.

One embodiment of the present invention relates to a method for removal of egg stains from a hard surface or from laundry, the method comprising contacting the egg stain-containing hard surface or the egg stain-containing laundry with a cleaning or detergent composition, preferably a laundry or dish wash composition, containing a metalloprotease of the invention.

Another embodiment relates a method for removing egg stains from fabric or textile which comprises contacting the fabric or textile with a cleaning or detergent composition, preferably a laundry or dish wash composition, comprising a metalloprotease of the invention.

A still further embodiment relates to a method for removing egg stains from fabric or textile which comprises contacting said a fabric or textile with a composition comprising a metalloprotease of the invention, wherein said composition further comprises at least one additional enzyme as set forth in the "other enzymes" section above, such as an enzyme selected from the group consisting of a carbohydrase, a peptidase, a protease, a lipase, a cellulase, a xylanase, a cutinase or a combination hereof.

In particular embodiments, the egg removing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, about 5.5 to about 9, preferably about 6 to about 8.5, and more preferably about 6 to about 8.

In particular embodiments, the egg removing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

The Invention is Further Summarized in the Below Paragraphs:

1. An isolated polypeptide having protease activity selected from the group consisting of:
   a. a polypeptide having at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99.1% sequence identity, at least 99.2% sequence identity, at least 99.3% sequence identity, at least 99.4% sequence identity, at least 99.5% sequence identity, at least 99.6% sequence identity, at least 99.7% sequence identity, at least 99.8% sequence identity, at least 99.9% sequence identity or even 100% sequence identity to the mature polypeptide of SEQ ID NO: 2;
   b. a polypeptide encoded by a polynucleotide that hybridizes under high stringency conditions with (i) the mature polypeptide coding sequence of SEQ ID NO: 1 or SEQ ID NO: 3 or (ii) the full-length complementary strand of (i);
   c. a polypeptide encoded by a polynucleotide having at least 85% sequence identity, at least 86% sequence identity, at least 87% sequence identity, at least 88% sequence identity, at least 89% sequence identity, at least 90% sequence identity, at least 91% sequence identity, at least 93% sequence identity, at least 94% sequence identity, at least 95% sequence identity, at least 96% sequence identity, at least 97% sequence identity, at least 98% sequence identity, at least 99%, at least 99.1% sequence identity, at least 99.2% sequence identity, at least 99.3% sequence identity, at least 99.4% sequence identity, at least 99.5% sequence identity, at least 99.6% sequence identity, at least 99.7% sequence identity, at least 99.8% sequence identity, at least 99.9% sequence identity or even 100% sequence identity to the mature polypeptide coding sequence of SEQ ID NO: 1;
   d. a variant comprising a substitution, deletion, and/or insertion of one or more (e.g. several) amino acids of the mature polypeptide of SEQ ID NO: 2; and
   e. a fragment of a polypeptide of (a), (b), (c), or (d) that has protease activity.

2. The polypeptide of paragraph 1, comprising or consisting of SEQ ID NO: 2 or the mature polypeptide of SEQ ID NO: 2.

3. The polypeptide of paragraph 2, wherein the mature polypeptide is amino acids 1 to 328 of SEQ ID NO: 2.

4. The polypeptide of any of paragraphs 1-3, which is a variant of the mature polypeptide of SEQ ID NO: 2 comprising a substitution, deletion, and/or insertion at one or more positions.

5. A composition comprising an isolated polypeptide having protease activity selected from the group consisting of:
   a. a polypeptide having at least 60% sequence identity, at least 65% sequence identity, at least 70% sequence identity, at least 75% sequence identity, at least 80% sequence identity, at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity or at least 99% sequence identity to the mature polypeptide of SEQ ID NO: 2;
   b. a polypeptide encoded by a polynucleotide that hybridizes under medium stringency conditions with (i) the mature polypeptide coding sequence of SEQ ID NO: 1 or SEQ ID NO: 3 or (ii) the full-length complementary strand of (i);
   c. a polypeptide encoded by a polynucleotide having at least 60% sequence identity, at least 65% sequence identity, at least 70% sequence identity, at least 75% sequence identity, at least 80% sequence identity, at least 85% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity or at least 99% sequence identity to the mature polypeptide coding sequence of SEQ ID NO: 1;
   d. a variant comprising a substitution, deletion, and/or insertion of one or more (e.g. several) amino acids of the mature polypeptide of SEQ ID NO: 2; and
   e. a fragment of a polypeptide of (a), (b), (c), or (d) that has protease activity.

6. An isolated polypeptide having protease activity selected from the group consisting of:
   a. a polypeptide having at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99.1% sequence identity, at least 99.2% sequence identity, at least 99.3% sequence identity, at least 99.4% sequence identity, at least 99.5% sequence identity, at least 99.6% sequence identity, at least 99.7% sequence identity, at least 99.8% sequence identity, at least 99.9% sequence identity or even 100% sequence identity to the mature polypeptide of the mature polypeptide of SEQ ID NO: 4;
   b. a polypeptide encoded by a polynucleotide that hybridizes under high stringency conditions with (i) the mature polypeptide coding sequence of SEQ ID NO: 3 or (ii) the full-length complementary strand of (i);
   c. a polypeptide encoded by a polynucleotide having at least 85% sequence identity, at least 86% sequence identity, at least 87% sequence identity, at least 88% sequence identity, at least 89% sequence identity, at least 90% sequence identity, at least 91% sequence identity, at least 93% sequence identity, at least 94% sequence identity, at least 95% sequence identity, at least 96% sequence identity, at least 97% sequence identity, at least 98% sequence identity, at least 99%, at least 99.1% sequence identity, at least 99.2% sequence identity, at least 99.3% sequence identity, at least 99.4% sequence identity, at least 99.5% sequence identity, at least 99.6% sequence identity, at least 99.7% sequence identity, at least 99.8% sequence identity, at least 99.9% sequence identity or even 100% sequence identity to the mature polypeptide coding sequence of SEQ ID NO: 3;
   d. a variant comprising a substitution, deletion, and/or insertion of one or more (e.g. several) amino acids of the mature polypeptide of SEQ ID NO: 4; and
   e. a fragment of a polypeptide of (a), (b), (c), or (d) that has protease activity.

7. The polypeptide of paragraph 1, comprising or consisting of SEQ ID NO: 4 or the mature polypeptide of SEQ ID NO: 4.

8. The polypeptide of paragraph 2, wherein the mature polypeptide is amino acids 1 to 290 of SEQ ID NO: 4.

9. The polypeptide of any of paragraphs 1-3, which is a variant of the mature polypeptide of SEQ ID NO: 4 comprising a substitution, deletion, and/or insertion at one or more positions.

10. A composition comprising an isolated polypeptide having protease activity selected from the group consisting of:
    a. a polypeptide having at least 60% sequence identity, at least 65% sequence identity, at least 70% sequence identity, at least 75% sequence identity, at least 80% sequence identity, at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity or at least 99% sequence identity to the mature polypeptide of the mature polypeptide of SEQ ID NO: 4;
    b. a polypeptide encoded by a polynucleotide that hybridizes under medium stringency conditions with (i) the mature polypeptide coding sequence of SEQ ID NO: 3 or (ii) the full-length complementary strand of (i);
    c. a polypeptide encoded by a polynucleotide having at least 60% sequence identity, at least 65% sequence identity, at least 70% sequence identity, at least 75% sequence identity, at least 80% sequence identity, at least 85% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity or at least 99% sequence identity to the mature polypeptide coding sequence of SEQ ID NO: 3;
    d. a variant comprising a substitution, deletion, and/or insertion of one or more (e.g. several) amino acids of the mature polypeptide of the mature polypeptide of SEQ ID NO: 4; and e. a fragment of a polypeptide of (a), (b), (c), or (d) that has protease activity.

11. The composition of paragraph 5 or 10, which is a detergent composition.

12. The detergent composition of paragraph 11, further comprising one or more additional enzymes selected among protease, lipase, cutinase, an amylase, carbohydrase, cellulase, pectinase, mannanase, arabinase, galactanase, xylanase, oxidase, e.g., a laccase, and/or peroxidase.

13. The detergent composition of any of paragraphs 5, 10-12, in form of a bar, a homogenous tablet, a tablet having two or more layers, a pouch having one or more compartments, powder (e.g. a regular or a compact powder), a granule, a paste, a gel, or a liquid (e.g. regular, compact or concentrated).

14. The detergent composition of any of paragraphs 5, 10-13, in form of a powder wherein the detergent composition is formulated such that, during use in aqueous cleaning operations, the wash water has a pH of from about 7 to about 11, from about 8 to about 11, from about 9 to about 11, or from about 9.5 to about 11.

15. Use of a composition according to any of the paragraphs 5, 10-14 in a cleaning process, such as laundry, hard surface cleaning, dish wash or automated dish wash.

16. A method of cleaning comprising contacting a surface and/or a fabric with the composition of any of the paragraphs 5, 10-15

17. The method of paragraph 16 wherein said a surface and/or a fabric comprises a grass stain and/or an egg stain.

18. An isolated polynucleotide encoding the polypeptide of any of paragraphs 1-4 and 6-9.

19. The polynucleotide of paragraph 18, wherein the polynucleotide is modified to correspond to the codon usage of a host cell intended for recombinant production of the enzyme 20. A nucleic acid construct or expression vector comprising the polynucleotide of any of paragraphs 18 or 19 operably linked to one or more control sequences that direct the production of the polypeptide in a host cell.

21. A recombinant host cell comprising the polynucleotide of any of paragraphs 12 or 13 operably linked to one or more control sequences that direct the production of the polypeptide.

22. A method of producing a polypeptide having protease activity, comprising:
  (a) cultivating the host cell of paragraph 21 under conditions conducive for production of the polypeptide; and
  (b) recovering the polypeptide.

EXAMPLES

Materials and Methods

Model Detergents

The model detergents B, J, M, and Y were used. Model detergent B is similar to a European type liquid detergent composition. Model detergent J is similar to a US type liquid detergent composition. Model detergent M is similar to a Chinese type powder detergent composition. Model detergent Y is similar to a Developing and Emerging (D&E) Asia Pacific market type powder detergent composition.

TABLE 1a

Laundry liquid model detergent B

| Compound | Content of compound (% w/w) | % active component (% w/w) |
|---|---|---|
| LAS | 7.20 | 7.0 |
| AEOS, SLES | 10.58 | 3.00Y |
| Soy fatty acid | 2.75 | 2.48 |
| Coco fatty acid | 2.75 | 2.80 |
| AEO | 6.60 | 6.60 |
| Sodium hydroxide | 1.05 | 1.1 |
| Ethanol/Propan-2-ol | 3.00 | 2.70/0.30 |
| MPG | 6.00 | 6.00 |
| Glycerol | 1.71 | 1.70 |
| TEA | 3.33 | 3.30 |
| Sodium formate | 1.00 | 1.00 |
| Sodium citrate | 2.00 | 2.00 |
| DTMPA | 0.48 | 0.20 |
| PCA | 0.46 | 0.18 |
| Phenoxy ethanol | 0.50 | 0.50 |
| $H_2O$, ion exchanged | 50.59 | 50.6 |

TABLE 1b

Laundry liquid model detergent J

| Compound | Content of compound (% w/w) | % active component (% w/w) |
|---|---|---|
| LAS | 5.15 | 5.00 |
| AS | 5.00 | 4.50 |
| AEOS | 14.18 | 10.00 |
| Coco fatty acid | 1.00 | 1.00 |
| AEO | 5.00 | 5.00 |
| MEA | 0.30 | 0.30 |
| MPG | 3.00 | 3.00 |
| Ethanol | 1.50 | 1.35 |
| DTPA (as Na5 salt) | 0.25 | 0.10 |
| Sodium citrate | 4.00 | 4.00 |
| Sodium formate | 1.00 | 1.00 |
| Sodium hydroxide | 0.66 | 0.66 |
| H2O, ion exchanged | 58.95 | 58.95 |

TABLE 1c

Laundry powder model detergent M

| Compound | % Component |
|---|---|
| Sodium sulfate | 41.23 |
| Sodium carbonate | 15 |
| Zeolite | 20 |
| Sodium silicate | 6 |
| LAS | 13.6 |
| AEO (7) | 1.92 |
| Polycarboxylate (Dow 445N) | 1 |
| FWA (CBS-X) | 0.05 |
| Perfume | 0.15 |

TABLE 1d

Laundry powder model detergent Y

| Compound | wt % component |
|---|---|
| Sodium sulfate | 42.1 |
| Sodium carbonate | 20 |
| Zeolite 4A (Silkem) | 15 |
| Sodium disilicate (Britesil H 265 LC) | 12 |
| Na-LAS granules (Marlon ARL) | 9.9 |
| Sokalan CP 5 Gran. | 1 |

Wash Assay
Automatic Mechanical Stress Assay (AMSA) for Laundry

In order to assess the wash performance in laundry washing experiments are performed, using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner. For further description see WO02/42740 especially the paragraph "Special method embodiments" at page 23-24.

The wash performance is measured as the brightness of the colour of the textile washed. Brightness can also be expressed as the intensity of the light reflected from the sample when illuminated with white light. When the sample is stained the intensity of the reflected light is lower, than that of a clean sample. Therefore the intensity of the reflected light can be used to measure wash performance.

Colour measurements are made with a professional flat-bed scanner (Kodak iQsmart, Kodak, Midtager 29, DK-2605 Brøndby, Denmark), which is used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int=\sqrt{r^2+g^2+b^2}.$$

The AMSA wash performance experiments were conducted under the experimental conditions specified below:

The grass stain swatch NZ Grass was prepared by applying juice from blended whole grass on WFK20A cotton/polyester.

The remaining swatches were obtained from Center for Testmaterials BV, P.O. Box 120, 3133 KT Vlaardingen, the Netherlands.

Protazyme OL Characterization Assay:
Substrate: Protazyme OL tablet (AZCL-collagen, Megazyme T-PROL 1000).
Temperature: Controlled (assay temperature).
Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0 and 11.0 with HCl or NaOH.

A Protazyme OL tablet is suspended in 2.0 ml 0.01% Triton X-100 by gentle stirring. 500 µl of this suspension and 500 µl assay buffer are dispensed in an Eppendorf tube and placed on ice. 20 µl protease sample (diluted in 0.01% Triton X-100) is added to the ice cold tube. The assay is initiated by transferring the Eppendorf tube to an Eppendorf thermomixer, which is set to the assay temperature. The tube is incubated for 15 minutes on the Eppendorf thermomixer at its highest shaking rate (1400 rpm). The incubation is stopped by transferring the tube back to the ice bath. Then the tube is centrifuged in an ice cold centrifuge for a few minutes and 200 µl supernatant is transferred to a microtiter plate. $OD_{650}$ is read as a measure of protease activity. A buffer blind is included in the assay (instead of enzyme).

Example 1. Cloning and Expression of M4 Metalloproteases from *Streptomyces thermoalcalitolerans* and *Lysobacter capsici*

The metalloprotease shown in SEQ ID NO: 2 was derived from a bacterial strain obtain from the German collection of

TABLE 2

| AMSA Experimental conditions | |
|---|---|
| Detergents | EU-type liquid model detergent B |
| | US-type liquid model detergent J |
| | Chinese-type powder model detergent M |
| | Developing and Emerging market-type powder model detergent Y |
| Detergent dose | 3.33 g/L for liquid model detergent B |
| | 0.79 g/L for liquid model detergent J |
| | 3.33 g/L for powder model detergent M |
| | 1.75 g/L for powder model detergent Y (with 0.035 g/L AEO added) |
| Test solution volume | 160 micro L |
| pH | pH is used "as is" in the current detergent solution and is not adjusted. |
| Wash time | 20 minutes |
| Temperature | 20° C., 30° C., or 40° C. |
| Water hardness | For wash with EU-type liquid model detergent B: |
| | 15° dH, adjusted by adding $CaCl_2 * 2H_2O$, $MgCl_2 * 6H_2O$ and $NaHCO_3$ (4:1:7.5) to milli-Q water. |
| | For wash with US-type liquid model detergent J: |
| | 6° dH, adjusted by adding $CaCl_2 * 2H_2O$, $MgCl_2 * 6H_2O$ and $NaHCO_3$ (2:1:4.5) to milli-Q water. |
| | For wash with Chinese-type powder model detergent M: |
| | 14° dH, adjusted by adding $CaCl_2 * 2H_2O$, $MgCl_2 * 6H_2O$ and $NaHCO_3$ (2:1:4.5) to milli-Q water. |
| | For wash with D&E market-type powder model detergent Y: |
| | 12° dH, adjusted by adding $CaCl_2 * 2H_2O$, $MgCl_2 * 6H_2O$ and $NaHCO_3$ (2:1:4.5) to milli-Q water. |
| Enzymes | M4 metalloprotease from *Streptomyces thermoalcalitolerans*. |
| | M4 metalloprotease from *Lysobacter capsici*. |
| | M4 metalloprotease from *Bacillus amyloliquefaciens*, also known as Neutrase ® |
| Enzyme concentration | 60 nM for model detergents B and J |
| | 100 nM for model detergents M and Y |
| Test materials | PC-05, Blood/milk/ink on cotton/polyester |
| | PC-03, Chocolate/milk/soot on cotton/polyester |
| | CS-37, Full egg/pigment on cotton |
| | NZ Grass, Grass stain on cotton/polyester |
| | EMPA117EH, Blood/milk/ink on cotton/polyester, extra heated |

Microorganisms and Cell Cultures (DSMZ) as DSM41741 type strain of *Streptomyces thermoalcalitolerans*. The strain was originally isolated from garden soil in Yogyakarta, Indonesia (Kim et al., Int. J. Syst. Bacteriol. (1999) 49: 7-17). Chromosomal DNA from a pure culture was purified and subjected to full genome sequencing using Illumina technology. The assembled genome sequence and subsequent analysis of the 16S ribosomal subunit gene sequences confirmed the identity of the strain as *Streptomyces thermoalcalitolerans*.

The genome sequence was analyzed for metalloproteases from the MEROPS family M4 by comparison to the M4 protease NprE from *B. subtilis* 168 (Uniprot P68736) by search using the BLAST program. This analysis identified a gene encoding a putative M4 metalloprotease with the nucleotide sequence given in SEQ ID: 1.

The gene encoding the M4 metalloprotease was amplified by PCR and fused with regulatory elements and homology regions for recombination into the *B. subtilis* genome.

The linear integration construct was a SOE-PCR fusion product (Horton, R. M., Hunt, H. D., Ho, S. N., Pullen, J. K. and Pease, L. R. (1989) *Engineering hybrid genes without the use of restriction enzymes, gene splicing by overlap extension Gene* 77: 61-68) made by fusion of the gene between two *Bacillus subtilis* chromosomal regions along with strong promoters and a chloramphenicol resistance marker. The SOE PCR method is also described in patent application WO 2003095658.

The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence.

The gene was expressed with a *Bacillus clausii* secretion signal (encoding the following amino acid sequence: MKKPLGKIVASTALLISVAFSSSIASA) replacing the native secretion signal. Furthermore the expression construct results in the addition of a carboxy-terminal poly histidine tail consisting of 6 consecutive histidine residues.

The SOE-PCR product was transformed into *Bacillus subtilis* and integrated in the chromosome by homologous recombination into the pectate lyase locus. Subsequently a recombinant *Bacillus subtilis* clone containing the integrated expression construct was grown in liquid culture. The culture broth was centrifuged (20000×g, 20 min) and the supernatant was carefully decanted from the precipitate and used for purification of the enzyme.

The gene encoding the metalloprotease shown in SEQ ID NO: 4 was derived applying the same procedure except that the donor was a *Lysobacter capsici* strain obtained from DSMZ as DSM19286 originally isolated from a rhizosphere sample of pepper, South Korea, Jinju.

Example 2. Characterization of the M4 Protease from *Streptomyces thermoalcalitolerans*: pH-Activity, pH-Stability, and Temperature-Activity The Protazyme OL characterization assay was used for obtaining the pH-activity profile at 37° C., the pH-stability profile (residual activity after 2 hours at indicated pH-values) and the temperature-activity profile at pH 8. For the pH-stability profile the protease was diluted 7× in the different characterization assay buffers to reach the pH-values of these buffers and incubated for 2 hours at 37° C. After incubation, the pH was adjusted to pH 8, before assay for residual activity, by dilution in pH 8 assay buffer.

The results are shown in Tables 3-5 below. Data for Neutrase (M4 protease from *Bacillus amyloliquefaciens*) are included in the tables. For Table 3, the activities are relative to the optimal pH for the enzymes. For Table 4, the activities are residual activities relative to a sample, which was kept at stable conditions (5° C., pH 8). For Table 5, the activities are relative to the optimal temperature at pH 8 for the enzyme.

TABLE 3 pH-activity profile at 37° C.

| pH | M4 protease from *Streptomyces thermoalcalitolerans* | M4 protease from *Bacillus amyloliquefaciens* |
|---|---|---|
| 2 | 0.00 | — |
| 3 | 0.02 | 0.01 |
| 4 | 0.07 | 0.02 |
| 5 | 0.46 | 0.46 |
| 6 | 0.41 | 0.91 |
| 7 | 0.44 | 1.00 |
| 8 | 0.96 | 0.53 |
| 9 | 1.00 | 0.14 |
| 10 | 0.23 | 0.06 |
| 11 | 0.06 | 0.04 |

TABLE 4 pH-stability profile (residual activity after 2 hours at 37° C.)

| pH | M4 protease from *Streptomyces thermoalcalitolerans* | M4 protease from *Bacillus amyloliquefaciens* |
|---|---|---|
| 2 | 0.00 | 0.02 |
| 3 | 0.00 | 0.00 |
| 4 | 0.71 | 0.01 |
| 5 | 0.99 | 0.98 |
| 6 | 1.08 | 0.99 |
| 7 | 1.09 | 0.95 |
| 8 | 1.07 | 1.04 |
| 9 | 1.04 | 0.98 |
| 10 | 0.05 | 0.87 |
| 11 | 0.00 | 0.12 |
| After 2 hours at 5° C. | 1.00 (at pH 8) | 1.00 (at pH 7) |

TABLE 5

Temperature activity profile

| Temp (° C.) | M4 protease from *Streptomyces thermoalcalitolerans* (pH 8) | M4 protease from *Bacillus amyloliquefaciens* (pH 7) |
|---|---|---|
| 15 | 0.08 | 0.14 |
| 25 | 0.24 | 0.26 |
| 37 | 0.69 | 0.91 |
| 50 | 1.00 | 1.00 |
| 60 | 0.98 | 0.73 |
| 70 | 0.70 | 0.26 |
| 80 | 0.07 | — |

Example 3. SDS-PAGE and N-Terminal Sequencing of the M4 Protease from *Streptomyces thermoalcalitolerans*

The relative molecular weight as determined by SDS-PAGE was approximately 37 k Da for the protease shown in SEQ ID NO: 2. The molecular weight determined by Intact molecular weight analysis was 35282.7 Da ((M+H)+ peak). The mature sequence (from EDMAN N-terminal sequencing data and Intact MS data) for the *Streptomyces* protease is shown in Table 6. The calculated molecular weight for this mature sequence was 35279.8 Da (and the calculated molecular weight for the (M+H)+ peak was 35280.8 Da).

Table 6 lists the found N-terminal sequences and the mature sequences deduced from the N-terminal sequences and intact mass measurements.

TABLE 6

Translated sequence, N-terminal sequence and mature sequence of the M4 protease from Streptomyces thermoalcalitolerans.

| Translated sequence | N-terminal sequence | Mature sequence |
|---|---|---|
| M4 protease from Streptomyces thermoalcalitolerans | GTGRTLY | GTGRTLYSGTVTLSTTRSGSTYQLYDTTRGGHRTYN-LARGTSGTGTLFTDADDVWGTG-TASSSSSDQTAAADAAYGAQVTWDFYKNVFGRNGIRN-NGTAAYSRVHYGNNYINAFWSDSCFCMTYGDGAGNVK-PLTSLDVAGHEMSHGLTSYTAGL-RYSGESGGLNEATSDIFGTGVEFYANNASDPGDYLIGEKID-INGNGTPLRYMDRPSKDGASADYWSSGVGNRDVHYSSGVAN HFFYLLAEGSGAKTINGVSYNSPTYDGSRITGIGRD-KALQIWYKALTTYMTSTTTYKGARTATLNAAAALYGSG-STEYNTVAAAWTAVNVT |

Example 4. AMSA Wash Performance of M4 Proteases from Streptomyces thermoalcalitolerans and Lysobacter capsici The wash performances of the M4 proteases from Streptomyces thermoalcalitolerans and from Lysobacter capsici were tested at different wash temperatures on various technical stains. The experiments were conducted as described above in the AMSA for laundry method using a single cycle wash procedure, with the swatches and the experimental conditions as specified in the tables below.

In liquid laundry detergent, good wash performance was observed using the Streptomyces thermoalcalitolerans metalloprotease and the Lysobacter capsici metalloprotease, both of which performed similarly to Neutrase® on the PC-05 (Blood/milk/ink on cotton/polyester) stain in the EU-type model detergent B. This indicates potential for use in surfactant-reduced detergent systems (Table 7).

In US-type liquid model detergent J, the metalloproteases from Streptomyces thermoalcalitolerans and from Lysobacter capsici both performed similarly to Neutrase® on grass stain (NZ Grass) (table 7). All tested metalloproteases displayed high wash performances on the egg stain CS-37 with more than 2½ times the S8 serine protease Savinase® wash performance in liquid model detergents B and J.

TABLE 7

AMSA data for metalloproteases from Streptomyces thermoalcalitolerans and from Lysobacter capsici in delta intensity units and relative to prior art protease Neutrase ®.
Conditions: 60 nM protease, 20 minutes wash.
For EU type liquid laundry detergent (model B, 60% surfactant level) 3.33 g/L, there was used 15° dH (4:1:7.5 $Ca^{2+}:Mg^{2+}:HCO_3^-$).
For US type liquid laundry detergent (model J, 100% surfactant level) 0.79 g/L, there was used 6° dH (2:1:4.5 $Ca^{2+}:Mg^{2+}:HCO_3^-$).

| | Model detergent B 40° C. | | | Model detergent J 30° C. | | | |
|---|---|---|---|---|---|---|---|
| | PC-03 | PC-05 | CS-37 | PC-03 | PC-05 | CS-37 | NZ Grass |
| Delta intensity | | | | | | | |
| Streptomyces thermoalcalitolerans protease | 14 | 34 | 51 | 5 | 10 | 34 | 3 |
| Lysobacter capsici protease | 17 | 30 | 51 | 7 | 8 | 37 | 3 |

TABLE 7-continued

AMSA data for metalloproteases from *Streptomyces thermoalcalitolerans* and from *Lysobacter capsici* in delta intensity units and relative to prior art protease Neutrase ®.
Conditions: 60 nM protease, 20 minutes wash.
For EU type liquid laundry detergent (model B, 60% surfactant level) 3.33 g/L, there was used 15° dH (4:1:7.5 $Ca^{2+}:Mg^{2+}:HCO_3^-$).
For US type liquid laundry detergent (model J, 100% surfactant level) 0.79 g/L, there was used 6° dH (2:1:4.5 $Ca^{2+}:Mg^{2+}:HCO_3^-$).

|  | Model detergent B 40° C. | | | Model detergent J 30° C. | | | |
| --- | --- | --- | --- | --- | --- | --- | --- |
|  | PC-03 | PC-05 | CS-37 | PC-03 | PC-05 | CS-37 | NZ Grass |
| Relative performance to Neutrase ® | | | | | | | |
| *Streptomyces thermoalcalitolerans* protease | 0.6 | 1.0 | 0.8 | 0.2 | 0.4 | 0.6 | 0.8 |
| *Lysobacter capsici* protease | 0.8 | 0.8 | 0.8 | 0.2 | 0.3 | 0.6 | 1.0 |

On the EMPA117EH (Blood/milk/ink on cotton/polyester, extra heated) swatch the metalloproteases from *Streptomyces thermoalcalitolerans* and from *Lysobacter capsici* both displayed fair wash performances at standard pH of the model detergent B wash solution (around pH 7.5). When the pH was adjusted to 9.5, however, Neutrase® lost almost all wash performance while the wash performances of the metalloproteases from *Streptomyces thermoalcalitolerans* and from *Lysobacter capsici* both surprisingly increased (table 8). This indicates potential for use in alkaline detergent systems, such as in most powder based detergent systems.

TABLE 8

AMSA data for metalloproteases from *Streptomyces thermoalcalitolerans* and from *Lysobacter capsici* in delta intensity units and relative to prior art protease Neutrase ®.
Conditions: EU type liquid laundry detergent (model B, 60% surfactant level) 3.33 g/L, 15° dH (4:1:7.5 $Ca^{2+}:Mg^{2+}:HCO_3^-$), 60 nM protease, 20 minutes, EMPA117EH (Blood/milk/ink on cotton/polyester, extra heated), 20° C.

|  | Model detergent B 20° C. | Model detergent B 20° C., pH 9.5 |
| --- | --- | --- |
| Delta intensity on EMPA117EH | | |
| *Streptomyces thermoalcalitolerans* protease | 16 | 32 |
| *Lysobacter capsici* protease | 13 | 22 |
| Relative performance to Neutrase ® | | |
| *Streptomyces thermoalcalitolerans* protease | 0.5 | 33.1 |
| *Lysobacter capsici* protease | 0.4 | 22.5 |

Both of the metalloproteases from *Streptomyces thermoalcalitolerans* and from *Lysobacter capsici* showed surprisingly good wash performance in powder detergent wash solution, under which conditions the prior art metalloprotease Neutrase® has very low wash performance (table 9).

In the Chinese-type powder model detergent M, the *Streptomyces thermoalcalitolerans* metalloprotease surpassed the wash performance by Neutrase® by more than forty times. The *Lysobacter capsici* metalloprotease unexpectedly surpassed the wash performance by Neutrase® by more than twenty times in the powder model detergent M.

In the Developing and Emerging Market-type powder model detergent Y the *Streptomyces thermoalcalitolerans* metalloprotease surpassed the wash performance by Neutrase® by more than 26 times at both temperatures tested. The *Lysobacter capsici* metalloprotease surpassed the wash performance by Neutrase® by more than 13 times at both temperatures tested in the powder model detergent Y. This shows potential for use in alkaline detergent systems, as well as potential for use in powder-derived detergent systems (table 9).

TABLE 9

AMSA data for metalloproteases from *Streptomyces thermoalcalitolerans* and from *Lysobacter capsici* in delta intensity units and relative to prior art protease Neutrase ®.
Conditions: 100 nM protease, 20 minutes wash, PC-05 (blood/milk/ink on cotton/polyester).
For Chinese type powder laundry detergent (model M, 80% surfactant level) 3.33 g/L, there was used 14° dH (2:1:4.5 $Ca^{2+}:Mg^{2+}:HCO_3^-$).
For D&E market type powder laundry detergent (model Y, 60% surfactant level) 1.75 g/L with 0.035 g/L AEO, there was used 12° dH (2:1:4.5 $Ca^{2+}:Mg^{2+}:HCO_3^-$).

|  | Model detergent M | Model detergent Y | |
| --- | --- | --- | --- |
|  | 20° C. | 20° C. | 40° C. |
| Delta intensity on PC-05 | | | |
| *Streptomyces thermoalcalitolerans* protease | 31 | 24 | 46 |
| *Lysobacter capsici* protease | 16 | 12 | 26 |
| Relative performance to Neutrase ® | | | |
| *Streptomyces thermoalcalitolerans* protease | 41.1 | 26.7 | 30.1 |
| *Lysobacter capsici* protease | 20.9 | 13.5 | 17.0 |

The invention claimed is:

1. A detergent composition suitable for laundry or dishwashing, the detergent composition comprising an isolated polypeptide having protease activity and a surfactant, wherein the isolated polypeptide having protease activity is selected from the group consisting of:
   a) a polypeptide having at least 95% sequence identity to the mature polypeptide of SEQ ID NO: 2, or the mature polypeptide of SEQ ID NO: 4;
   b) a polypeptide encoded by a polynucleotide having at least 95% sequence identity to the mature polypeptide coding sequence of SEQ ID NO: 1 or SEQ ID NO: 3; and
   c) a fragment of a polypeptide of (a) or (b) that has protease activity, wherein the detergent composition is in the form of a powder, a tablet, or a granule.

2. The detergent composition of claim 1, further comprising one or more additional enzymes selected among a protease, a lipase, a cutinase, an amylase, a carbohydrase, a cellulase, a pectinase, a mannanase, an arabinase, a galactanase, a xylanase, an oxidase, a laccase, a peroxidase, and any combination thereof.

3. The detergent composition of claim 1, in the form of a powder wherein the detergent composition is formulated such that, during use in aqueous cleaning operations, the wash water has a pH of from about 7 to about 11.

4. A method of cleaning comprising contacting a surface or a fabric with the composition of claim 1.

5. The method of claim 4 wherein said surface or fabric comprises a grass stain, an egg stain, or both a grass stain and an egg stain.

6. An isolated polynucleotide encoding a polypeptide having protease activity, wherein the polypeptide having protease activity is selected from the group consisting of
   a) a polypeptide having at least 95% sequence identity to the mature polypeptide of SEQ ID NO: 2, or the mature polypeptide of SEQ ID NO: 4;
   b) a polypeptide encoded by a polynucleotide having at least 95% sequence identity to the mature polypeptide coding sequence of SEQ ID NO: 1 or SEQ ID NO: 3; and
   c) a fragment of a polypeptide of a) or b) that has protease activity, wherein the polynucleotide is modified to correspond to the codon usage of a host cell intended for recombinant production of the enzyme wherein the polynucleotide is operably linked to one or more control sequences that direct the production of the polypeptide in a host cell.

7. A nucleic acid construct or expression vector comprising the polynucleotide of claim 6.

8. An isolated recombinant host cell comprising the polynucleotide of claim 6 operably linked to one or more control sequences that direct the production of the polypeptide.

9. A method of producing a polypeptide having protease activity, comprising:
   (a) cultivating the host cell of claim 8 under conditions conducive for production of the polypeptide; and
   (b) recovering the polypeptide.

10. The composition of claim 1, wherein the polypeptide has at least 97% sequence identity to the mature polypeptide of SEQ ID NO: 2 or the mature polypeptide of SEQ ID NO: 4.

11. The composition of claim 1, wherein the polypeptide has at least 99% sequence identity to the mature polypeptide of SEQ ID NO: 2 or the mature polypeptide of SEQ ID NO: 4.

12. The composition of claim 1, wherein the polypeptide has at least 97% sequence identity to a polypeptide encoded by to the mature polypeptide coding sequence of SEQ ID NO: 1 or the mature polypeptide coding sequence of SEQ ID NO: 3.

13. The composition of claim 1, wherein the polypeptide has at least 99% sequence identity to a polypeptide encoded by to the mature polypeptide coding sequence of SEQ ID NO: 1 or the mature polypeptide coding sequence of SEQ ID NO: 3.

14. The composition of claim 1, further comprising a builder.

15. The composition of claim 1, wherein the mature polypeptide is amino acids 1 to 328 of SEQ ID NO: 2 or amino acids 1 to 290 of SEQ ID NO: 4.

16. The composition of claim 1, wherein the polypeptide is a variant of the mature polypeptide of SEQ ID NO: 2, or of the mature polypeptide of SEQ ID NO: 4, the variant comprising any combination of a substitution, a deletion, or an insertion at one or more positions.

17. The polynucleotide of claim 6, wherein the polypeptide has at least 97% sequence identity to the mature polypeptide of SEQ ID NO: 2 or the mature polypeptide of SEQ ID NO: 4.

18. The polynucleotide of claim 6, wherein the polypeptide has at least 99% sequence identity to the mature polypeptide of SEQ ID NO: 2 or the mature polypeptide of SEQ ID NO: 4.

19. The polynucleotide of claim 6, wherein the polypeptide has at least 97% sequence identity to a polypeptide encoded by to the mature polypeptide coding sequence of SEQ ID NO: 1 or the mature polypeptide coding sequence of SEQ ID NO: 3.

20. The polynucleotide of claim 6, wherein the polypeptide has at least 99% sequence identity to a polypeptide encoded by to the mature polypeptide coding sequence of SEQ ID NO: 1 or the mature polypeptide coding sequence of SEQ ID NO: 3.

21. A detergent composition formulated as a powder, a tablet, or granule, the detergent composition comprising an isolated polypeptide having protease activity and a surfactant, wherein the isolated polypeptide having protease activity is selected from the group consisting of:
   (a) a polypeptide having at least 95% sequence identity to the mature polypeptide of SEQ ID NO: 2, or the mature polypeptide of SEQ ID NO: 4;
   (b) a polypeptide encoded by a polynucleotide having at least 95% sequence identity to the mature polypeptide coding sequence of SEQ ID NO: 1 or SEQ ID NO: 3; and
   (c) a fragment of a polypeptide of (a) or (b) that has protease activity.

* * * * *